(12) United States Patent
Bohner et al.

(10) Patent No.: US 11,939,565 B1
(45) Date of Patent: Mar. 26, 2024

(54) METHODS AND SYSTEMS FOR PERFORMING BIOTECHNOLOGICAL PROCESSES

(71) Applicant: Trisk Bio Ltd., Stevenage (GB)

(72) Inventors: Gergo Bohner, Cambridge (GB); Adam Luke Hiles, Leighton Buzzard (GB); Samuel Isidor Jones, London (GB); Kevin Lynagh, Tacoma, WA (US); Ryan Olf, Cambridge (GB); Gabor Pap, Stevenage (GB); Spencer Ryan Wilson, London (GB); Thomas Felix Martin Cummings, London (GB)

(73) Assignee: Trisk Bio Ltd., Stevenage (GB)

( * ) Notice: Subject to any disclaimer, the term of this patent is extended or adjusted under 35 U.S.C. 154(b) by 0 days.

(21) Appl. No.: 18/215,393

(22) Filed: Jun. 28, 2023

(51) Int. Cl.
  *C12M 1/34* (2006.01)
  *C12M 1/12* (2006.01)
  *C12M 1/36* (2006.01)

(52) U.S. Cl.
  CPC ............ *C12M 41/40* (2013.01); *C12M 37/00* (2013.01); *C12M 41/44* (2013.01); *C12M 41/48* (2013.01)

(58) Field of Classification Search
  CPC ...... C12M 41/40; C12M 37/00; C12M 41/44; C12M 41/48
  See application file for complete search history.

(56) References Cited

U.S. PATENT DOCUMENTS

| | | | |
|---|---|---|---|
| 2003/0040104 A1* | 2/2003 | Barbera-Guillem | C12M 23/48 435/286.2 |
| 2012/0089930 A1* | 4/2012 | Stanton, IV | C12M 29/20 715/763 |
| 2016/0040112 A1* | 2/2016 | Coppeta | C12M 27/18 435/293.1 |
| 2018/0371399 A1* | 12/2018 | Griffin | C12M 29/14 |
| 2021/0002602 A1* | 1/2021 | Ludlam | B01L 3/5085 |
| 2021/0102156 A1* | 4/2021 | Griffin | C12M 29/04 |

(Continued)

OTHER PUBLICATIONS

Benjamin Adams et al., "Moving from the bench towards a large scale, industrial platform process for adeno-associated viral vector purification," Regeneron Pharmaceuticals Inc., Jun. 20, 2020.

(Continued)

*Primary Examiner* — William H. Beisner
*Assistant Examiner* — Danielle B Henkel
(74) *Attorney, Agent, or Firm* — Weiss & Arons LLP

(57) ABSTRACT

Provided herein is a method for incubating living cells, in accordance with principles of the disclosure, may include the steps of: (a) providing a pressurized gas to a medium reservoir, the pressurized gas providing an impetus that moves a growth medium in the medium reservoir to a bioreactor chamber via a first incoming fluid line connecting the medium reservoir to the bioreactor chamber; (b) simultaneously or subsequently to step (a), providing a pressurized gas to a cell reservoir holding a suspension of the living cells, the pressurized gas providing an impetus that moves the suspension to the bioreactor chamber via a second incoming fluid line connecting the cell reservoir to the bioreactor chamber; and (c) incubating the growth medium and the living cells in the bioreactor chamber, under conditions compatible with cell viability.

11 Claims, 21 Drawing Sheets

Making a liquid addition to the bioreactor

Taking a liquid sample from the bioreactor

(56) References Cited

U.S. PATENT DOCUMENTS

2022/0326248 A1* 10/2022 Miltenyi ................ C12M 23/28

OTHER PUBLICATIONS

Hillebrandt N. et al., "Integrated Process for Capture and Purification of Virus-Like Particles: Enhancing Process Performance by Cross-Flow Filtration," Frontiers in Bioengineering and Biotechnology, Published: May 25, 2020.
Arvind Srivastava et al., "Manufacturing Challenges and Rational Formulation Development for AAV Viral Vectors," Journal of Pharmaceutical Sciences, Apr. 2, 2021.

* cited by examiner

METHODS AND SYSTEMS FOR PERFORMING BIOTECHNOLOGICAL PROCESSES

FIELD OF TECHNOLOGY

Aspects of the disclosure relate to methods for conducting biotechnological processes, for example cell culture and virus growth and purification.

BACKGROUND

Bioreactor set up and assembly, for example for cell culture for virus production or harvesting the cells themselves, can be labor intensive. For reusable bioreactors, individual components must be manually cleaned, assembled, leak tested, sterilized and cooled before every batch. Even for single-use bioreactors, connections must be manually made, significantly contributing to downtime between runs. Efficient use requires planning the entire process in advance, in order to make the necessary connections. Making process adjustments in real time may be very challenging, since doing so typically involves manual changes to the bioreactor connectivity. Furthermore, the significant reliance on manual assembly and disassembly of connections introduces potential for human error in adherence to the specified parameters, proper sterile technique, and audit trail documentation.

SUMMARY OF THE DISCLOSURE

It is an object of the present disclosure to provide a more adaptable system architecture for biotechnological processes, for example incubation and expansion of eukaryotic cells.

It is a further object of the present disclosure to decrease downtime between bioreactor runs.

It is a further object of the present disclosure to provide a system for biotechnological processes that enables process modification without extensive modification of tubing and wiring.

It is a further object of the present disclosure to provide an apparatus for biotechnological processes that enables process modification by simple replacement of portable modules or components thereof.

It is a further object of the present disclosure to provide a system for biotechnological processes that enables fully or largely automated process execution.

It is a further object of the present disclosure to provide an integrated solution for upstream and downstream steps for biotechnological processes, such as incubation of virus-producing cells, lysis, and downstream virus purification steps.

The present disclosure improves upon conventional approaches by providing a system of interconnected tanks and rigid and flexible tubing for gas, steam, and liquid, some aspects of which can be steam sterilized and maintained as a closed system accessed only via controlled interfaces. The sterilization and controlled interfaces enable the system to maintain a sterile boundary between the internal flow paths and the external environment, preventing external contamination and corruption of sensitive biological material. The interfaces are amenable to robotic attachment and detachment.

The system includes a bioreactor to which sterile additions can be made, and sterile samples can be drawn from. Maintenance of sterility enables an uncontaminated cell culture process to run successfully within the bioreactor.

Additions to and samples from the bioreactor may be actuated using compressed, sterile air, which pressurizes a liquid-containing tank and induces liquid flow out of the tank into a downstream container (e.g., a bioreactor or sample container). These processes may be automated.

Air used for transferring liquids in this way can be sterilized by passage through sterile filters. These filters themselves may be steam sterilized and tested for filter integrity via automated processes.

In an exemplary process, the bioreactor is populated with cells, which grow and divide under controlled conditions. Cells are used to produce a molecule of interest or other product, e.g., recombinant virus particles. The bioreactor is stirred and contains pH, dissolved oxygen, and temperature sensors, which are used to trigger additions of acid, base, air, carbon dioxide, and warming, to maintain optimum cell health in culture. These additions may be performed using pressurized air-driven flow, as described above.

An apparatus in accordance with principles of the disclosure may include a central component and a peripheral component. The central compartment or component may include, and/or be at least partially bounded by, an interface, which may be referred to as a central-side interface, via which the central compartment or component interacts with the peripheral component. The apparatus may be configured for cell culture. The cell culture may be for the purpose of virus production. The cell culture may be for the purpose of cell harvesting. The apparatus may be configured for other biotechnological processes known to those skilled in the art.

The central compartment may also include: (i) one or more pressure actuators; (ii) multiple outgoing pressure lines connecting the one or more pressure actuators to the central-side interface; (iii) a bioreactor chamber; and (iv) a plurality of incoming fluid lines connecting the central-side interface to the bioreactor chamber. The bioreactor chamber may be configured to house the living cells and a growth medium.

The mentioned peripheral compartment may include: (i) multiple fluid storage containers; (ii) multiple incoming pressure lines; and (iii) multiple outgoing fluid lines. Each fluid storage container may be operably connected to at least one incoming pressure line and at least one outgoing fluid line, which means, in some embodiments, that an incoming pressure line can be used to exert pressure on the interior of the fluid storage container to which it is connected, and an outgoing fluid line can be used to convey fluid out of the fluid storage container to which it is connected. When connected, an impetus originating from the pressure actuator(s) (which may be conveyed by pressure) may serve to move fluid (e.g., buffers and other fluids required for cell incubation, cell suspensions, a virus inoculum, and the like) from reagent tanks or container in the peripheral compartments into the bioreactor chamber. The amounts of reagents moved may be predetermined according to a set program.

DETAILED DESCRIPTION

Figure 1:
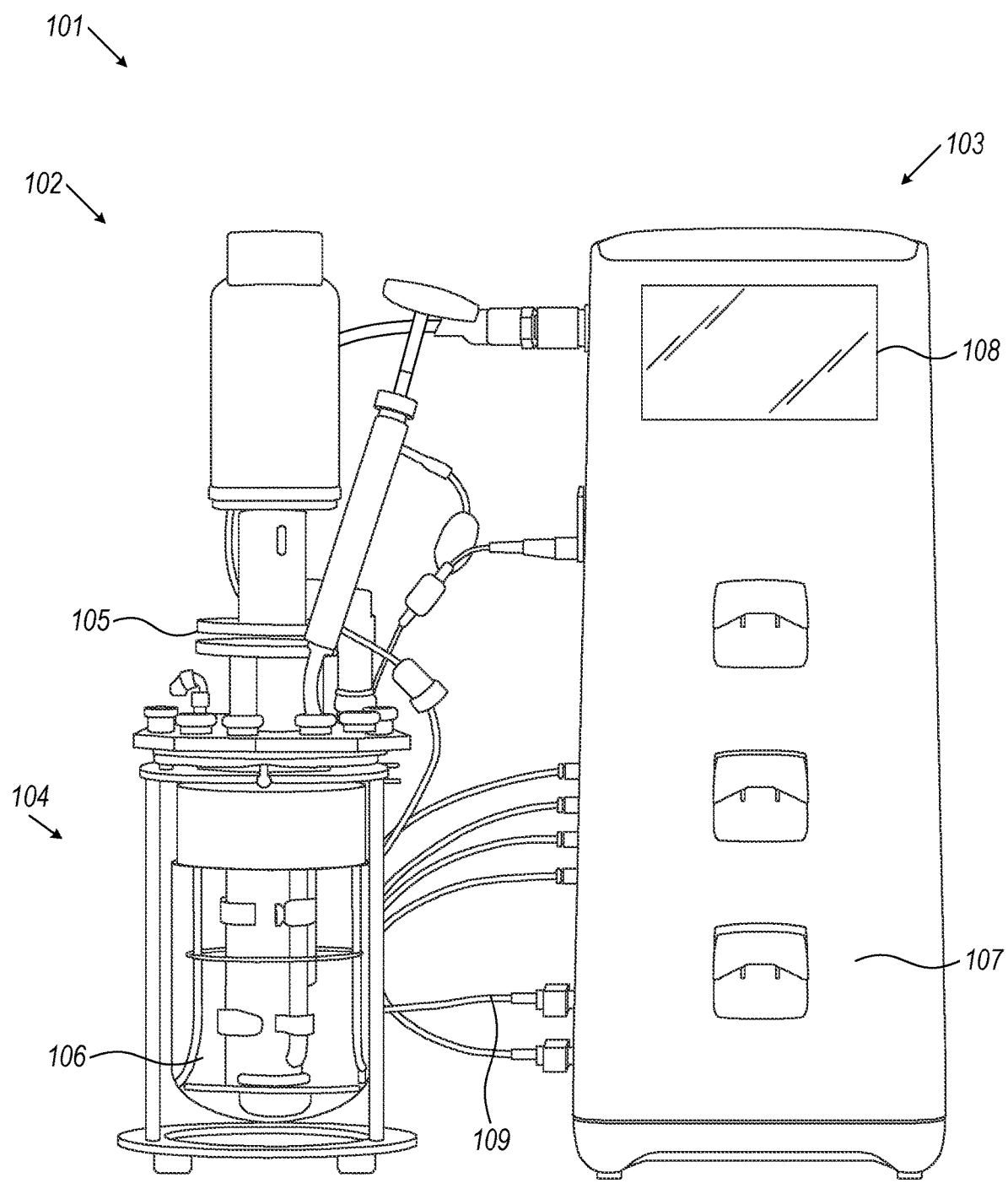
FIG. 1 depicts a side view of a prior art bioreactor system.

Provided herein is an apparatus, in accordance with principles of the disclosure. The apparatus may include a central compartment or component and a peripheral compartment or component. The central compartment or component may include, and/or be at least partially bounded by, an interface, which may be referred to as a central-side interface, via which the central compartment or component interacts with the peripheral compartment or component. The apparatus may be configured for cell culture. The cell culture may be for the purpose of virus production. The cell culture may be for the purpose of cell harvesting. The apparatus may be configured for other biotechnological processes known to those skilled in the art.

The terms central and peripheral, when referring to compartments or components, do not necessarily imply centrality or peripherality with regard to a particular central landmark or vantage point. In some embodiments, the central compartment(s) may be fixed (e.g., floor mounted or wall mounted), while the peripheral compartment(s) may be portable. The peripheral compartment(s) may be moved or toggled between one or more central compartments, reuse compartments, or the like, by detaching it/them (if attached), moving it/them to a different fixed compartment, and attaching it/them to the new fixed compartment. This process may be largely or fully automated. The peripheral compartment(s) may be sized such that they are movable by a cell culture robot. A cell culture robot may be sized to operate in a room designed for cell culture or other biotechnological processes. In some embodiments, the peripheral compartment(s) may be supported by a shelf or portable cart configured for such use.

The central compartment may also include any or all of: (i) one or more pressure actuators; (ii) multiple (e.g., at least 2) outgoing pressure lines connecting the one or more pressure actuators to the central-side interface; (iii) a bioreactor chamber; and (iv) a plurality of incoming fluid lines connecting the central-side interface to the bioreactor chamber. The bioreactor chamber may be configured to house the living cells and a growth medium.

In some embodiments, the pressure actuator(s) are pressure regulator(s). In some embodiments, a pressure regulator is used as a pressure source in the described methods. The pressure regulator may be programmatically set to a predetermined pressure level by a controller. If the set pressure level is greater than the pressure in a proximal air line, which is disposed downstream relative to the actuator, pressured air flows through the proximal air line. A selector valve may be present that allows either air, steam, or cleaning fluid to flow into the filter. If air flow is selected, pressurized air may proceed to the air-sterilizing filter. The filter may be operably connected to a vent, a drain, a pressure sensor, and a temperature sensor. In some embodiments, pressurized air proceeds through a sterile air line downstream of the filter to a head space of a reagent container, which may be, in some embodiments, a medium reservoir or a reservoir of another liquid reagent (e.g., a reagent needed for a biotechnological process). In some embodiments, increased pressure in the head space impels an amount, which may be predetermined amount, of the container's fluid contents out of the container, through a downstream fluid line, and into a fluid destination container.

Those skilled in the art will appreciate that the specific growth medium used is not critical for carrying out the described methods. Growth medium may refer to any medium or buffer compatible with cell survival and/or replication. Growth medium may include basal medium_ and a supplement, for example serum or a cocktail of growth factors. Solely for exemplification, certain suitable growth media for eukaryotic cells include Minimum Essential Medium Eagle, ADC-1, LPM (Bovine Serum Albumin-free), FIO(HAM), F12 (HAM), DCCM1, DCCM2, RPMI 1640, RPMI 1641, BGJ Medium (with and without Fitton-Jackson Modification), Basal Medium Eagle (B ME—with the addition of Earle's salt base), Dulbecco's Modified Eagle's Medium (DMEM, Sigma), Iscove's Modified Dulbecco's Medium, McCoy's 5A Medium, and Leibovitz's L-15 Medium. A chemically defined, serum-free media e.g., EXCELL™ 300 Series medium (JRH Biosciences, Lenexa, Kans.) may also be used.

In some embodiments, the outgoing pressure lines lead from the pressure actuators to the interface and are configured to transmit pressure from the pressure actuators to their termini in the central-side interface. To this end, the pressure actuator(s) may be operably connected with the outgoing pressure lines.

In some embodiments, the incoming fluid lines lead from the interface to the bioreactor chamber and are configured to transport fluid originating in fluid storage containers (described below) from the central-side interface to the bioreactor chamber.

Optionally, the central compartment is at least partially enclosed or bounded by a housing. In some embodiments, the central compartment is fully enclosed by a housing. It is not required, in some embodiments of the disclosure, for all the compartments of the central compartment to be enclosed within a single housing. In a non-limiting illustrative example, the outgoing pressure lines, bioreactor chamber, and incoming fluid lines may be contained within a housing, while the pressure actuator(s) may reside outside the housing and be operably connected with the outgoing pressure lines contained within the housing. In some embodiments, the described central-side interface may form part of the housing and/or be contiguous with the housing. The described outgoing pressure lines and incoming fluid lines may contain termini that reside within the housing and/or the central-side interface. The housing may serve as a barrier to reduce exposure of its internal parts to contaminants from the outside, for example dust and other particulate matter. In some embodiments, the housing is airtight at ambient pressure.

In some embodiments, the central compartment may be configured for cleaning, sterilization and reuse. For example, it may be possible to clean sterilize the central compartment (e.g., as described herein) and subsequently use it for additional incubations.

In some embodiments, the central compartment can be sterilized by connecting it to a peripheral compartment configured for this purpose. This sterilizing peripheral component may have an interface similar to the peripheral compartment interfaces described herein, but instead of reagent containers, it includes conduits that directly connect the interfaces to one another in a loop fashion. Accordingly, a cleaning medium or solution and/or a sterilization medium (for example steam) can be successively run through the central component, thereby cleaning and sterilizing its internal components (e.g., conduits, valves, connectors, etc.). In some embodiments, the filters are also sterilized via this process. In some embodiments, selector valves are used to direct cleaning solutions instead of compressed air through the filters and other components (see, for example, FIGS. 23-24). The central component may now be ready for use in performing a biotechnological process.

The mentioned peripheral compartment may include any or all of: (i) multiple (e.g., at least 2) fluid storage containers; (ii) multiple incoming pressure lines; and (iii) multiple outgoing fluid lines. Each of the fluid storage containers may be operably connected to at least one incoming pressure line and at least one outgoing fluid line, which means, in some embodiments, that an incoming pressure line can be used to exert pressure on the interior of the fluid storage container to which it is connected, and an outgoing fluid line can be used to convey fluid out of the fluid storage container to which it is connected. When connected, an impetus originating from the pressure actuator(s) (which may be conveyed by a pressurized gas) may serve to move fluids from reagent tanks or containers in the peripheral compartments into the bioreactor chamber. Non-limiting examples of fluids that may be present in the fluid storage contains are buffers (e.g., bicarbonate), anti-foaming agents, and other fluids required for cell incubation; a cell suspension, a virus inoculum, a lysis reagent, and a nuclease (non-limiting examples of which are endonucleases sold under the trade name Benzonase®). The amounts of reagents moved may be predetermined according to a set program.

The peripheral compartment may be configured for sterilization, cleaning, and reuse. The peripheral compartment may be attachable to a reuse compartment. The reuse compartment may include: (i) one or more pressure actuators; (ii) multiple (e.g., at least 2) outgoing pressure lines connecting the pressure actuators to an interface for connecting to a peripheral component; and (iii) a plurality of incoming fluid lines connecting the interface to the bioreactor chamber. In some embodiments, the peripheral compartment is configured for automated sterilization, cleaning, and subsequent refilling and reuse.

In some embodiments, there is provided herein a system, including the described peripheral compartment and the described reuse compartment. In some embodiments, the reuse compartment includes any of the components described herein for the central compartment.

Each of the incoming pressure lines may be configured to sterilely and reversibly connect to one of the outgoing pressure lines. In some embodiments, the connection is via a described interface. In some embodiments, the apparatus is configured for connection and disconnection of interfaces to be largely, or fully, automated.

Each of the outgoing fluid lines may be configured to sterilely and reversibly connect to one of the incoming fluid lines. In some embodiments, the connection is via a described interface. In some embodiments, the apparatus is configured for connection and disconnection of interfaces to be largely, or fully, automated.

Sterilely may refer to a connection that excludes access of microbes to the interior of the mentioned lines. Reversibly may refer to a connection that can be dismantled, while preserving the structure of the mentioned lines and their ability to be cleaned and reused in a sterile, closed system.

In embodiments of the described methods and systems, the connectors joining the ingoing and outgoing fluid lines may be hydraulic connectors. The connectors may be configured to automatically shut off liquid flow when disconnected. The connectors may be spring loaded or use other technologies known in the art, for example ball bearings, to enable automatic shutoff. The connectors may be quick couplings. They may include a floating ball valve that closes automatically when the coupling ends are disconnected from one another. In some embodiments, the connections may be able to withstand at least 10 bar pressure.

In some embodiments, the connectors may be flat-face hydraulic connectors. Connecting the ends may engage the movement of internal springs. Disconnecting the ends may automatically close the lumen. This mechanism may act as an automatic valve.

In some embodiments, the connectors are no-spill, no-drip, or dry break connectors. In some embodiments, the connectors are configured to impede air ingress into the flow path during connection and disconnection. Alternatively, or in addition, the connectors are configured to impede liquid egress from the flow path during connection and disconnection.

In some embodiments, the connectors are internally valved. In other embodiments, the connectors are externally valved.

The connectors joining the ingoing and outgoing pressure lines for the described methods and systems may be, in some embodiments, pneumatic couplings. The couplings may include two parts. The two parts may be the quick coupling, or the female part, and the plug-in, nipple, or male part. The coupling may close the line automatically when the coupling ends are disconnected from one another. This may impede loss of pressurize from the system. The connectors may be configured to automatically shut off liquid flow when disconnected. The connectors may be spring loaded or use other technologies known in the art, for example ball bearings, to enable automatic shutoff. The connectors may be quick couplings. They may include a floating ball valve that closes automatically when the coupling ends are disconnected from one another. In some embodiments, the connections may be able to withstand at least 10 bar pressure.

In some embodiments, the connectors may be flat-face pneumatic connectors. Connecting the ends may engage the movement of internal springs. Disconnecting the ends may automatically close the lumen. This mechanism may act as an automatic valve.

In some embodiments, the pneumatic connectors are no-spill, no-drip, or dry break connectors. In some embodiments, the connectors are configured to impede air ingress into the flow path during connection and disconnection. Alternatively, or in addition, the connectors are configured to impede liquid egress from the flow path during connection and disconnection.

In some embodiments, the connectors are internally valved. In other embodiments, the connectors are externally valved.

The peripheral compartment may also include a peripheral-side interface, which may be configured to mate with the described central-side interface.

The peripheral compartment may be at least partially enclosed by a peripheral compartment housing. In some embodiments, the peripheral compartment is fully enclosed by a peripheral compartment housing. In some embodiments, the described peripheral-side interface may form part of the housing and/or be contiguous with the housing. The described incoming pressure lines and outgoing fluid lines may contain termini that reside within the housing and/or the peripheral-side interface. The housing may serve as a barrier to reduce exposure of its internal parts to contaminants from the outside, for example dust and other particulate matter. In some embodiments, the peripheral compartment housing is airtight at ambient pressure.

The peripheral component may also include any combination of sensors and/or valves. In some embodiments, the sensors are fluid sensors. In some embodiments, fluid sensors may be configured to monitor fluid transfers within the system. In some embodiments, the valves may be associated with any of the described fluid lines; for example, the outgoing fluid lines. In some embodiments, the valves may be configured to prevent retrograde movement of fluid within the system. In some embodiments, a processing unit may be operably connected to the fluid sensors. The processing unit may be configured to generate, or create, an audit trail. The audit trail may include a record of the sequence and timing of fluid transfers within the system.

Returning to the central compartment, the central component may also include any combination of sensors and/or valves. The sensors may include fluid sensors. In some embodiments, the fluid sensors may be configured to monitor fluid transfers within the system. In some embodiments, the valves may be associated with any of the described fluid lines; for example, the incoming fluid lines. In some embodiments, the valves may be configured to prevent retrograde movement of fluid within the system. In some embodiments, a processing unit may be operably connected to the fluid sensors. The processing unit may be configured to generate, or create, an audit trail. The audit trail may include a record of the sequence and timing of fluid transfers within the system.

The central compartment may be fixedly connected to supplies of gases (e.g., compressed air), steam, and/or cleaning fluids. Alternatively, or in addition, the peripheral compartments) may be not fixedly connected to any supplies of gases (e.g., compressed air), steam, and/or cleaning fluids. Fixedly may refer to a connection not intended to be disassembled and assembled on an ongoing basis, as will be appreciated by those skilled in the art.

The bioreactor chamber may be made of stainless steel and may, in some embodiments, be reusable. The bioreactor chamber may be made of glass and may, in some embodiments, be reusable. In some embodiments, the bioreactor chamber may be made of plastic and may, in some embodiments, be disposable.

In some embodiments, the bioreactor chamber may have a capacity of 15 liters or less, for example 1-15 liters, 2-15 liters, 3-15 liters, 5-15 liters, 1-10 liters, 2-10 liters, 3-10 liters, 1-5 liters, 2-5 liters, or 3-5 liters. In some embodiments, the bioreactor chamber may be made of stainless steel and have a capacity of 10 liters or less, for example 1-10 liters, 2-10 liters, 3-10 liters, 5-10 liters, 1-5 liters, 2-5 liters, or 3-5 liters. In some embodiments, the bioreactor chamber may be made of glass and have a capacity of 10 liters or less, for example 1-10 liters, 2-10 liters, 3-10 liters, 5-10 liters, 1-5 liters, 2-5 liters, or 3-5 liters. The described technology may facilitate use of reusable bioreactors at this scale, for example by their decreased downtime between runs and/or increased process agility.

In some embodiments, each of the outgoing pressure lines and incoming fluid lines includes a terminus, collectively referred to as central-side termini. The central-side termini may be arranged in a first essentially planar array, which is, in some embodiments, disposed in the central-side interface. The central-side interface may be described herein as a central-side connector, which may be configured to mate with, or be juxtaposed to, a peripheral-side connector having a corresponding spatial arrangement, e.g., a mirror image of the arrangement of the central-side connector.

In some embodiments, each of the incoming pressure lines and outgoing fluid lines includes a terminus, collectively referred to as peripheral-side termini. The peripheral-side termini may be arranged in a second essentially planar array, which is, in some embodiments, disposed in a peripheral-side interface. The peripheral-side interface may be described herein as a peripheral-side connector, which may be configured to mate with, or be juxtaposed to, the central-side connector.

Each of the central-side termini may be configured to mate, or connect, with a corresponding peripheral-side terminus. The interface or connector may be configured to consummate the connection in a multi-step process, for example, including the steps of (a) enclosing the termini within an enclosure resistant to pathogen entry; (b) sterilizing the interior of the enclosure; and (c) fluidly connecting the termini pairs. Sterility of the enclosure may be maintained until step (c) is completed. Step (a) may be preceded by juxtaposing (but not yet fluidly connecting) the corresponding terminus pairs. In some embodiments, each enclosure contains individual pairs of termini. In some embodiments, an enclosure encompasses multiple pairs of termini.

In some embodiments, the central compartment comprises filters that are configured to deliver a sterile gas (e.g., air) in pressurized form through one of 2-3 interfaces into tanks. The pressure may impel fluid to flow from the tanks into the bioreactor. In additional embodiments, the central compartment may be configured to reverse the air flow for sampling from the bioreactor, namely to supply air through sterile filters into the bioreactor, moving fluid from the reactor across one of the interfaces and into a sample tank disposed in a described peripheral compartment (see, e.g., FIG. 5). In some embodiments, the central compartment may be configured to support steaming, monitoring, and testing of any of the herein-described components. In some embodiments, the described system is more readily cleanable compared to a peristaltic pump system. In some embodiments, use of a pressurized gas reduces mechanical failure modes.

The central compartment may be connected to one or more utility lines or conduits which contain or supply air, a sterilizing medium (e.g., a sterilizing gas) and/or a cleaning medium (e.g., a cleaning fluid). The central compartment may be connected to additional lines which contain or supply additional compartments, for example water, diluting buffers, etc. In certain embodiments, the additional lines supply 2 or more components selected from ambient air, carbon dioxide, steam, purified water, and cleaning solution. In other embodiments, 3 or more of the aforementioned components, 4 or more of the aforementioned components, or all 5 of the aforementioned components are supplied to the central compartment by lines to which the component is connected. In some embodiments, the connection is a fixed connection.

Those skilled in the art will appreciate that a non limiting list of sterilizing media includes steam, dry heat, ethylene oxide, vaporized hydrogen peroxide, chlorine dioxide as, vaporized peracetic acid, and nitrogen dioxide. The sterilizing medium may be a gas, e.g., a heated gas. The sterilizing medium may be steam.

The cleaning medium may be a cleaning fluid. The cleaning fluid may include detergents or surfactants (for example, anionic detergents or cationic detergents). Solutions of acids (e.g., citric acid, hydrochloric acid, or acetic acid) or bases (e.g., NaOH) may also be used as cleaning solutions.

The central compartment may additionally include a pressure-driven (or pressurized) product sampling line or conduit, connecting the bioreactor chamber to a sample container. The sampling line may lead from the bioreactor chamber to the sample container and be configured to transfer a sample from the bioreactor chamber to the sample container. In some embodiments, the sample container is disposed in the central compartment. In some embodiments, the sample container is disposed in the peripheral compartment. In some embodiments, the sample container is disposed in an additional central compartment. In some embodiments, the sample container is disposed in an additional peripheral compartment.

In some embodiments, differential pressure is used to impel the sample out of the chamber. In some embodiments, the bioreactor is operably connected to a positive pressure line configured to impel a sample out of the bioreactor, as described generally herein for fluid movement via pressurized air. In other embodiments, the sample container is operably connected to a negative pressure, or vacuum, line, which may create negative pressure in the interior of the sample container, thereby drawing a sample from the bioreactor chamber to the sample container.

In some embodiments, the peripheral compartment (or an additional peripheral compartment, if more than one is utilized) also includes a virus container, a third incoming pressure line connected to the virus container, and a third outgoing fluid line connected to the virus container. In other embodiments, a polynucleotide container, containing a polynucleotide solution, is present instead of a virus container. In other embodiments, a polynucleotide container, containing a polynucleotide solution, is present in addition to a virus container, either in the same peripheral compartment (e.g., in different containers) or in a different peripheral compartment. A corresponding outgoing pressure line(s) and an incoming fluid line(s) may be present in the central compartment and configured to mate with the virus and/or polynucleotide container-associated lines.

In some embodiments, the polynucleotide is a vector required for the desired biotechnological process. Non-limiting examples are polynucleotides encoding viruses for purposes of virus production; and polynucleotides encoding factors necessary for viral reproduction. Other examples of polynucleotides are vectors encoding proteins, either intracellular or secreted, desired to be harvested at the conclusion of the process. In some embodiments, the polynucleotide may be a plasmid, recombinant virus, cosmid, or artificial chromosome. Plasmid refers to a circular double-stranded DNA loop into which other DNA segments can be ligated. Another type of vector is a viral vector, in which other DNA segments can be ligated to the viral genome. In some embodiments, an engineered vector contains an origin of replication, multiple cloning sites, and a selectable marker. The vector itself may be a nucleotide sequence, typically a DNA sequence, that contains an insert (transgene) sequence and a larger sequence that serves as the "backbone" or "principal chain" of the vector. In other embodiments, the vector includes a promoter to facilitate expression of the transgene. Polynucleotides are optionally mixed with a transfection reagent.

In some embodiments, the peripheral compartment (or an additional peripheral compartment, if more than one is utilized) also includes a virus container, a third incoming pressure line connected to the virus container, and a third outgoing fluid line connected to the virus container. A corresponding outgoing pressure line and an incoming fluid line may be present in the central compartment and configured to mate with the virus container-associated lines.

Also provided is a method for incubating living cells, in accordance with principles of the disclosure. The method may include the steps of providing a pressurized gas to a medium reservoir (or container), the pressurized gas providing an impetus that moves a growth medium in the medium reservoir to a bioreactor chamber via a first incoming fluid line connecting the medium reservoir to the bioreactor chamber. The method may also include the step of providing a pressurized gas to a cell reservoir (or container) holding (or including) a suspension of the living cells, the pressurized gas providing an impetus that moves the suspension to the bioreactor chamber via a second incoming fluid line connecting the cell reservoir to the bioreactor chamber. In various embodiments, this step may be performed simultaneously or subsequently the previous step (e.g., providing a pressurized gas to a medium reservoir). The method may also include the step of incubating the growth medium and the living cells in the bioreactor chamber, under conditions compatible with cell viability.

It is clarified that the described method does not require that all the growth medium in the medium reservoir be transported to the bioreactor chamber. Those skilled in the art will appreciate that an appropriate amount of growth medium for the desired cell incubation will typically be added to the bioreactor, and the skilled person will know how much is required, based on general principles of cell culture. In some embodiments, the method includes removing spent medium from the bioreactor chamber and replenishing the chamber with approximately an equal volume of fresh medium, as needed during the cell culture process.

In some embodiments, the pressurized gas used in the method is a biologically compatible gas, for example nitrogen, oxygen, carbon dioxide, or a mixture thereof. In some embodiments, the pressurized gas is ambient air. In some embodiments, the pressurized gas is sterile filtered, for example sterile-filtered air. In some embodiments, the filters have been sterilized (e.g., via steam), and filter integrity has been tested, prior to commencing the described method.

In some embodiments, the filters impel air through one of 1-3 interfaces into reagent containers or tanks, which in turn drives fluid to flow into the bioreactor. In some embodiments, the sampling process uses a reverse air flow path. Air may be supplied through sterile filters into the bioreactor, moving fluid from the reactor across one of the interfaces and into a sample tank.

In some embodiments, the pressurized gas used in step (b) of the method is the same as that used in step (a). In other embodiments, a different pressurized gas is used in step (b) vs. step (a). In other embodiments, an additional pulse of the same pressurized gas is used in step (b) vis-à-vis step (a).

In some embodiments, the medium within the bioreactor chamber may be equilibrated, prior to adding the cell suspension to the bioreactor chamber. Equilibration may include bringing the medium temperature and/or pH to desired values or ranges. In some embodiments, the equilibration is an automated process. Subsequent detection of sufficient equilibration and addition of cells to the medium may also be automated.

The described medium reservoir and cell reservoir may each also be associated with an incoming pressure line, which serves to conduct the pressurized gas. Each incoming pressure line in the peripheral component may be connected (e.g., via an interface) to an outgoing pressure line disposed in a separate compartment (such as the described central compartment) and/or surrounded by a separate housing, the outgoing pressure lines conveying pressure from a pressure actuator to the incoming pressure lines. Each actuator may be connected to one or multiple pressure lines.

After leaving the described medium reservoir and cell reservoir and before entering the described first and second incoming fluid lines (respectively), the medium and/or cell suspension may pass through outgoing fluid lines. The outgoing fluid lines may be disposed in the same compartment or housing as the medium and cell reservoirs. The incoming fluid lines may be disposed in the same compartment or housing as the bioreactor chamber. The separate compartments may be connected via an interface.

The method may include the additional step of monitoring fluid transfer via flow sensor(s). In some embodiments, the sensors are disposed in the first (or central) compartment described herein. In some embodiments, at least some of the sensors are disposed in the first or central compartment. In some embodiments, the described method may include the additional step of generating an audit trail via a processing unit operably connected to the fluid sensors. In some embodiments, the sensors monitor transfers of the medium and the cell suspension into the bioreactor chamber. In other embodiments, the sensors monitor transfer of the virus inoculum into the bioreactor chamber. In other embodiments, the sensors monitor additional infusions of fresh medium into the bioreactor chamber, for example, during continued cell incubation. In other embodiments, the sensors monitor transfers of other solutions necessary for the biotechnological process. In other embodiments, the sensors monitor transfer(s) of sample(s) from the bioreactor chamber to a sampling container during the biotechnological process. In other embodiments, the sensors monitor transfer of a lysate component to the bioreactor chamber. In other embodiments, the sensors generally monitor transfer of fluids moved during the biotechnological process, in order to generate an audit trail. Each of the aforementioned embodiments are combinable.

In some embodiments, the method further includes the step of monitoring the mass of the bioreactor, combined with the contents therein. The bioreactor may be connected to a mass-measurement device (which may be, e.g., a scale or the like) to continuously or periodically monitor the mass inside the bioreactor (which can be calculated by subtracting the combined mass of the bioreactor with its contents, minus the known mass of the empty bioreactor). In some embodiments, tracking the bioreactor mass is used to monitor flow rates of solutions and samples into and out of (respectively) the bioreactor. In some embodiments, this information is used to ensure a desired combined biomass and solution volume inside the bioreactor.

In some embodiments, pH, dissolved oxygen, temperature sensors in the bioreactor are transmitted to a processor. Based on this information, the processor controls additions of acidic or basic additives, oxygen, and/or carbon dioxide; heating, and stirring, to maintain cell health in the culture. These additions may be driven using pressurized air-driven flow, as described.

In some embodiments, the peripheral compartment or module (which may be the "slow" addition module/first peripheral compartment shown in the figures) contains tanks holding liquid supplies to be added to the bioreactor, in a manner that maintains the sterility of the steam sterilized station.

In some embodiments, an additional peripheral compartment or module (which may be the "fast" addition module/additional peripheral compartment shown in the figures) constitutes a mechanism for attaching smaller modules in order to make relatively quick and small volume additions to the bioreactor. Alternatively or in addition, the fast module is used to take samples. In some embodiments, the fast module is configured to allow small modules to be attached and removed more often than the slow module. In some embodiments, the additional peripheral compartment is configured to be steam-sterilized and water cooled, for example as described herein, to speed up the connection process.

In some embodiments, the additional peripheral compartment(s) include cooling channels that surround the steam chambers. The cooling channels may be between 0.5-3 millimeters, between 0.5-2 millimeters, between 0.5-1.5 millimeters, between 0.8-3 millimeters, between 0.8-2 millimeters, or between 0.8-1.5 millimeters in diameter (measured from the outer walls of the steam chamber outward). In some embodiments, the cooling channels may be in the configuration of a water jacket. In some embodiments, the cooling channels are configured to actively pump water though them, thus enabling rapid cooling of a peripheral compartment after steam sterilization.

Figure 5:
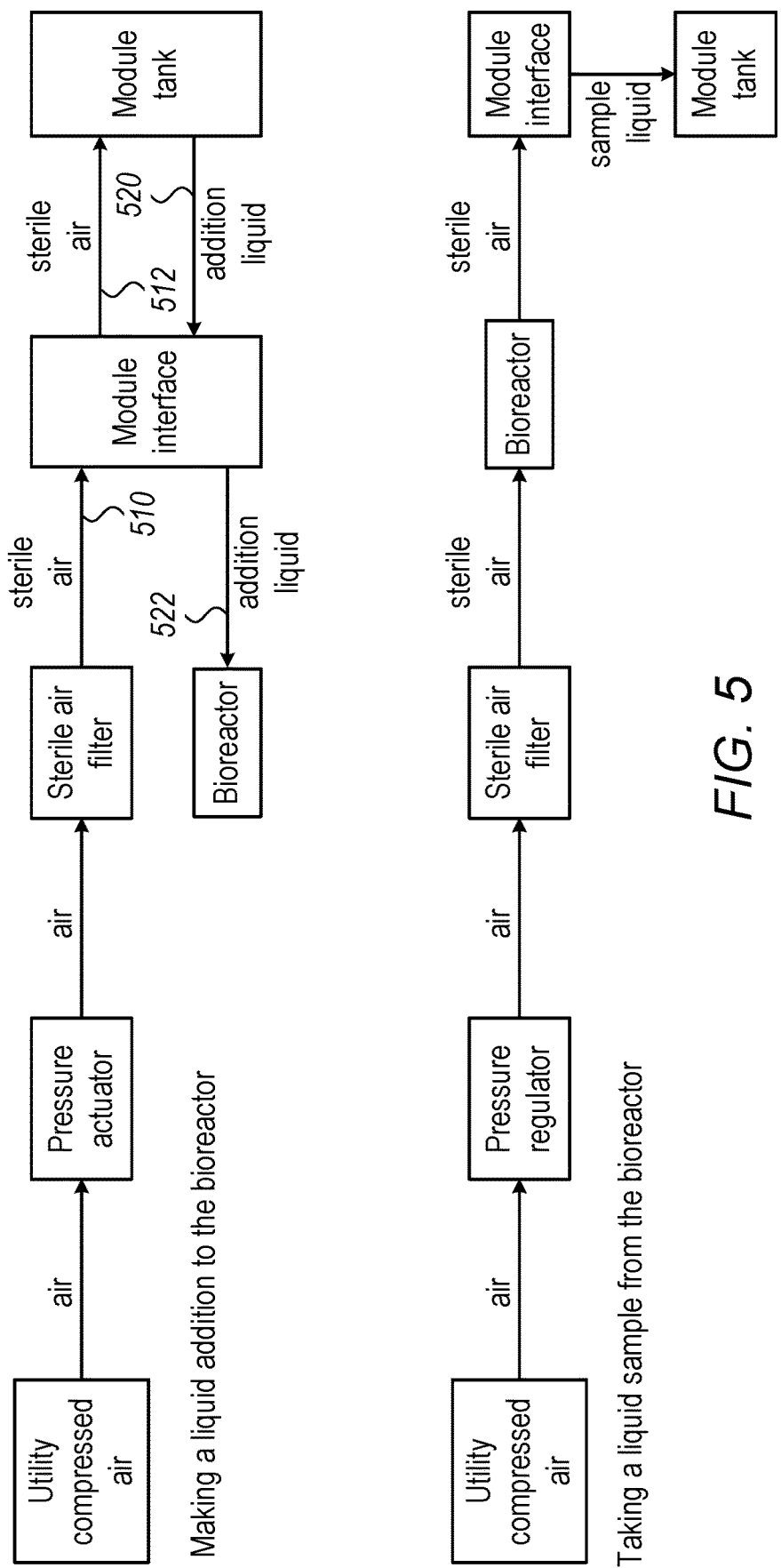
FIG. 5 is a schematic diagram of air flow for making additions to and taking samples from a bioreactor.

In some embodiments, the described method also includes an additional step of moving a sample of contents of the bioreactor chamber to a sample container via exertion of differential pressure on the bioreactor chamber. The sample may be conveyed via a product sampling line, connecting or leading from the bioreactor chamber to the sample container. In some embodiments, the sample container is operably connected to a negative pressure line (e.g., separate from the product sampling line and connected via a separate aperture from the product sample line) which transmits negative pressure to the bioreactor chamber. In other embodiments, a positive pressure line connected to the bioreactor (e.g., via compressed air, for example as depicted in FIG. 5) is utilized. Sampling may be conducted at multiple intervals, as necessary to monitor one or more environmental conditions, cell metabolite levels or production milestones. Any of the former may be used to inform process adjustments, for example pH adjustment, medium replenishment, or product harvesting.

In some embodiments, the described pressure actuator(s) produce the described pressurized gas; and the first and second pressure lines transmit the pressurized gas to the medium and cell reservoirs (e.g., respectively).

The method may include the additional step of programming a processor to execute a predetermined, choreographed fluid transfer program, e.g., via instructing the actuator(s) to move predetermined amounts of selected fluids at predetermined time intervals. Alternatively or in addition, the processor instructs the actuator(s) to execute fluid transfers based on predetermined milestones, such as a desired cell density, viral particle density, or metabolic indicator. The system may be configured to automatically detect these milestones and determine the timing of each process stage accordingly.

In some embodiments, the bioreactor chamber of the described method may be disposed in a first compartment, the first compartment including: (i) one or more pressure actuators; (ii) a first outgoing pressure line; (iii) a second outgoing pressure line; (iv) the mentioned first and second incoming fluid lines.

The medium reservoir and cell reservoir may be disposed in one or more additional compartments, the additional compartment(s) also including: (i) a first incoming pressure line connected to the medium reservoir; (ii) a second incoming pressure line connected to the cell reservoir; (iii) a first outgoing fluid line connected to the medium reservoir; and (iv) a second outgoing fluid line connected to the cell reservoir. In some embodiments, the aforementioned reservoirs and lines are all contained within a single compartment. At least two compartments, including the first compartment, may thus be present.

In some embodiments, the medium reservoir and its associated lines are contained within a first additional compartment, and the cell reservoir and its associated lines are contained within a second additional compartment. At least three compartments, including the first compartment, may thus be present.

In some embodiments, the second additional compartment (or one of the additional compartments) also includes a virus container, a third incoming pressure line connected to the virus container, and a third outgoing fluid line connected to the virus container. A corresponding outgoing pressure line and incoming fluid line may be present in the first compartment and configured to mate with the virus container-associated lines. In some embodiments, the first additional compartment houses the medium container and associated lines, and the second additional compartment houses the cell suspension and virus containers and their associated lines.

The described Step a) (namely providing a pressurized gas to a medium reservoir or container, e.g., as detailed above) may be preceded by the following prior steps pre-a1 and pre-a2, which may be performed in either order or simultaneously: Step pre-A1: sterilely connecting the first and second outgoing pressure lines to the first and second incoming pressure lines (e.g., respectively); and Step pre-A2: sterilely connecting the first and second outgoing fluid lines to the first and second incoming fluid lines (e.g., respectively).

In some embodiments, steps pre-A1 and pre-A2 are performed robotically. In some embodiments, all the connections contained within, or associated with, a particular interface are connected simultaneously. In some embodiments, simultaneous connection is performed automatically or robotically. In some embodiments, simultaneous connection of all connections within an interface enables a relatively rapid connection time. In some embodiments, an automated or robotic connection enables relatively precise process parameter control and/or an automated audit trail.

In some embodiments, steps pre-A1 and pre-A2 may involve a reversible connection. In some embodiments, a reversible connection may enable reuse of portable and/or peripheral compartments. In some embodiments, a reversible connection may enable process flexibility.

In some embodiments, there is provided a method of joining two pre-sterilized, closed systems, in accordance with principles of the disclosure. In some embodiments, the method comprises method steps and/or compositions described herein. In some embodiments, the method is automated.

Use of terminology such as "first and second outgoing pressure lines" is equivalent to referring to the first outgoing pressure line and the second outgoing pressure line, as appropriate for each such instance.

The first and second outgoing pressure lines and the first and second incoming fluid lines may terminate in central-side connectors. The first and second incoming pressure lines and the first and second outgoing fluid lines may terminate in peripheral-side connectors. One or both of the described steps referred to as pre-A1 and pre-A2 (connecting the various pressure and fluid lines, respectively) may include the sub-step of sterilizing the central-side connectors and the peripheral-side connectors via providing a sterilizing medium to the central-side connectors and the peripheral-side connectors. As described, in some embodiments, the sterilizing medium is a gas (e.g., steam). In some embodiments, the sterilizing gas is provided from a source connected to the aforementioned first/central compartment.

In some embodiments, the described method for incubating living cells also includes the step of disconnecting the first/central compartment from at least one of the additional peripheral compartments and/or connecting the first/central compartment to another additional peripheral compartments.

In some embodiments, the described method for incubating living cells also includes the step of connecting the first compartment to an additional peripheral compartment. In some embodiments, this additional compartment includes reagent containers and associated pressure and liquid conveyance lines. In some embodiments, the connecting step is performed robotically. In some embodiments, the connecting step includes any of the steps mentioned herein for connecting interfaces. In some embodiments, the connecting step is performed during the cell incubation step. In some embodiments, the second compartment and the additional compartment remain simultaneously connected to the first compartment for at least part of the execution.

In some embodiments, any of the described connecting and disconnecting steps are components of a choreographed programs for executing a biotechnological process, which may also include fluid transfer steps, as described.

In some embodiments, when multiple peripheral compartments are utilized, the described steps pre-A1 and pre-A2 may be performed separately for each peripheral compartment. In some embodiments, a first additional/peripheral compartment is connected to the first (central) compartment (including performing steps pre-A1 and pre-A2) prior to initiation of the process. In some embodiments, a second additional/peripheral compartment is connected to the first (central) compartment after process initiation. In some embodiments, the second additional/peripheral compartment is connected to the first (central) compartment via a separate interface from that used by the first additional/peripheral compartment.

The first additional/peripheral compartment may include all supplies necessary for initiating the process, for example medium components. Such supplies may remain connected to the main compartment for the duration of the process, for example for medium replenishment and the like. The second additional/peripheral compartment may include reagents added at particular timepoints, for example cells and viruses. The second additional/peripheral compartment may remain connected to the main compartment for the duration of the process. In other embodiments, the second additional/peripheral second compartment may be disconnected from the main compartment during the process. The second additional/peripheral compartment may be replaced by a third additional/peripheral compartment, utilizing the same interface. The second additional/peripheral compartment may contain reagents or components that are relatively labile. For example, the reagents or components in this compartment may not be able to withstand storage at ambient temperatures for the planned duration of the process, without significant loss in activity.

In some embodiments, the first and/or second additional/peripheral compartment may be replaced by a different peripheral compartment containing a set of reagents non-identical to the replaced compartment. In some embodiments, doing so enables facile process modifications in subsequent runs.

In some embodiments, the described method also includes the step of connecting the first compartment to an additional peripheral compartment. In some embodiments, this additional compartment also includes reagent containers and associated pressure and liquid conveyance lines. In some embodiments, the connecting step is performed robotically. In some embodiments, the connecting step includes any of the steps mentioned herein for connecting interfaces. In some embodiments, the connecting step is performed during the cell incubation step.

In some embodiments, the described method also includes a step of adding a lytic reagent to the bioreactor chamber via a pressure-driven line. The lytic reagent may be any ingredient used in cell lysis, including, for example, cell lytic enzymes, hypotonic buffer, detergents, and the like. In other embodiments, a mechanical lysis process is performed.

In some embodiments, the described method also includes a step of transporting a direct or indirect product of the cell incubation method to a harvest or downstream container. The product may be a cell lysate, intact cells, or another product. In various embodiments, the product may be transported via a product outlet line or conduit, which may be negative- or positive-pressure driven, as described. The harvest container may be disposed in a receiving compartment. In other embodiments, the receiving compartment is the aforementioned first (central) compartment. In other embodiments, the receiving compartment is another compartment that includes: (i) a pressure actuator; (ii) an outgoing pressure line; and (iii) an incoming fluid line.

In some embodiments, the receiving compartment is the aforementioned peripheral compartment or an additional peripheral compartment reversibly connectable to the first/central compartment. In other embodiments, the peripheral compartment is reversibly connectable to a different central compartment, which may refer to a compartment including (i) one or more pressure actuators; (ii) a plurality of outgoing pressure lines; (iii) a holding container; and (iv) a plurality of incoming fluid lines. A holding container may be configured to hold product during, or between, intermediate stages of downstream purification steps, e.g., filtration and chromatography steps. In some embodiments, the peripheral compartment may include: (i) a plurality of fluid storage containers; (ii) a plurality of incoming pressure lines; and (iii) a plurality of outgoing fluid lines. Use of a peripheral component to house a harvest or downstream container may enable facile transfer of product between upstream and downstream steps. In some embodiments, the method also includes the step of connecting the peripheral compartment to the described different central compartment.

In some embodiments, direct transport of the product to a container within the first/central compartment, or a similarly equipped compartment, enables seamless transition to downstream processing of the product. In some embodiments, the same hardware used for moving fluids for the cell incubation step(s) can be used to drive fluids for downstream processing steps (for example, as described in FIG. 24).

Also provided is a system, in accordance with principles of the disclosure. The system may include: (a) an apparatus, including a first compartment and a second compartment; and (b) a programmable robot configured to sterilely and reversibly connect the first compartment to the peripheral compartment. The connection may be via an interface, which may be any of the interfaces described herein. The act of connection may generate a workable apparatus for hosting a biotechnological process, for example cell incubation.

The first compartment may include: (i) one or more pressure actuators; (ii) a plurality of outgoing pressure lines; (iii) a bioreactor chamber; and (iv) a plurality of incoming fluid lines. The actuator(s) may be operably connected with the outgoing pressure lines.

The second compartment may include: (i) a plurality of fluid storage containers; (ii) a plurality of incoming pressure lines; and (iii) a plurality of outgoing fluid lines. Each of the fluid storage containers may be operably connected to at least one of the incoming pressure lines and at least one of the outgoing fluid lines.

The programmable robot may also be configured to connect the first compartment to a third compartment (e.g., via a separate interface), while the first compartment remains connected to the second compartment. The third compartment may include: (i) a plurality of fluid storage containers; (ii) a plurality of incoming pressure lines; and (iii) a plurality of outgoing fluid lines. Each of the fluid storage containers may be operably connected to at least one of the incoming pressure lines and at least one of the outgoing fluid lines.

In some embodiments, the programmable robot may also be configured to create an audit trail.

The mentioned outgoing pressure lines and incoming fluid lines may terminate in first compartment-side connectors arranged in a first array, which may be essentially planar. The incoming pressure lines and outgoing fluid lines may terminate in second compartment-side connectors arranged in a second array, which may be essentially planar.

The first array may have a spatial arrangement that mirrors the second array's spatial arrangement. In this way, the respective connectors in each array may be able to connect to one another.

Aforementioned embodiments of the first/central, second/peripheral, and additional peripheral compartments; components and contents thereof; interfaces between them; and methods for operating same may be applicable to the described system.

In other embodiments, in accordance with principles of the disclosure, a system may include a first apparatus or compartment, including a first sub-compartment and a second sub-compartment. The system may also include a downstream product line or conduit. The system may also include a second apparatus or compartment (which also may be referred to as a processing apparatus or compartment). In certain embodiments, the second apparatus may be a filtration apparatus and/or a chromatography apparatus.

In some embodiments, the downstream product line connects the bioreactor chamber to the second apparatus.

The first sub-compartment of the first apparatus may include: (i) one or more pressure actuators; (ii) a plurality of outgoing pressure lines; (iii) a bioreactor chamber; and (iv) a plurality of incoming fluid lines. The actuator(s) may be operably connected with the outgoing pressure lines. Aforementioned embodiments of the first/central compartment may be applicable to this system as well.

The second sub-compartment of the first apparatus may include: (i) a plurality of fluid storage containers; (ii) a plurality of incoming pressure lines; and (iii) a plurality of outgoing fluid line. Each of the fluid storage containers may be operably connected to at least one incoming pressure line and at least one outgoing fluid line. Aforementioned embodiments of the second/peripheral compartment, and optionally additional peripheral compartment(s), may be applicable to this system as well.

The described system may further include a programmable robot configured to sterilely and reversibly connect the first sub-compartment to the second sub-compartment.

In some embodiments, the first and second apparatuses may be within a single housing. In other embodiments, the first and second apparatuses may be enclosed in separate housings. In either case, the 2 apparatuses may share utilities, for example pressure actuators, utility lines, or the like.

With reference to the second apparatus, it will be appreciated that the terms filtration apparatus and chromatography apparatus are not intended to convey that the apparatus only performs filtration and/or chromatography. Rather, the terms denote an apparatus that is capable of performing at least filtration and/or chromatography, examples of which are filters and chromatography columns, respectively.

Filtration and chromatography are well-established techniques in virus capsid purification and other biotechnological processes. Their use is described throughout the literature, for example by Adams B et al. (Moving from the bench towards a large scale, industrial platform process for adeno-associated viral vector purification. Biotechnol. Bioeng. 2020, 117, 3199-3211), Srivastava A et al. (Manufacturing challenges and rational formulation development for AAV viral vectors. J. Pharm. Sci. 2021, 110, 2609-2624), Hillebrandt N et al. (Integrated Process for Capture and Purification of Virus-Like Particles: Enhancing Process Performance by Cross-Flow Filtration. Front. Bioeng. And Biotechnol. 2020, 8; https://doi.org/10.3389/fbioe.2020.00489), and other references.

Filtration refers to passage over a membrane that selects components on the basis of size. A non-limiting example of filtration is Tangential flow filtration (TFF), also known as cross-flow filtration.

Chromatography refers to passage through a substrate or column that selects components on the basis of size, affinity to column components, ionic charge, or other characteristics. A non-limiting example of chromatography is size-exclusion chromatography.

In some embodiments, chromatography is used to separate full or loaded from empty viral capsids. Such chromatography techniques are known in the art, and are described, for example, in Gagnon, Pete. (2009). Chromatographic Purification of Virus Particles. 10.1002/9780470054581.eib583.

The second apparatus may be configured to sterilely and reversibly connect to a peripheral processing sub-compartment, including: (i) a plurality of fluid storage containers; (ii) a plurality of incoming pressure lines; and (iii) a plurality of outgoing fluid lines. In this regard, it will be appreciated that the second apparatus may be used similarly to the first apparatus, in the sense that it may be reversibly connected to modules or peripheral compartments that provide reagents (which may be liquid reagents) necessary for (in the case of the second apparatus) filtration, chromatography, and/or other downstream steps. The peripheral processing sub-compartment need not differ in structure from the second sub-compartment of the first apparatus. In some embodiments, the second sub-compartment of the first apparatus houses reagents usable in cell culture, while the peripheral processing sub-compartment houses reagents usable for downstream processing.

In some embodiments, the second apparatus includes a first pressure actuator and a second pressure actuator, which may independently be pressure regulators, which is, in some embodiments, programmatically set to a predetermined pressure level by a controller. The first pressure actuator may be configured to generate a gaseous pressure pulse through a first downstream line, thereby pressurizing a first liquid container, resulting in exit of fluid from the container and movement of the fluid through the apparatus in a first direction (e.g., clockwise, when viewed from the front of the apparatus). The fluid may move through a conduit downstream from the container. The conduit may be selected from a filtration apparatus and a chromatograph apparatus.

The second pressure actuator may be configured to generate a gaseous pressure pulse through a second downstream line, thereby pressurizing a second liquid container, resulting in exit of fluid from the container and movement of the fluid through the apparatus in a second direction (e.g., counterclockwise, when viewed from the front of the apparatus). The fluid may move through the aforementioned conduit, but in the opposite direction to the aforementioned instance. See, e.g., FIG. 24.

The aforementioned embodiments of the first/central, second/peripheral, and additional peripheral compartments; components and contents thereof; interfaces between them; and methods for operating same may be applicable to the described system.

Also provided herein is an interface sterilization process for joining two sterilized, closed systems in a sterile fashion, in accordance with principles of the disclosure. In some embodiments, the two systems each have an interface, including conduits with fluidly connectable ends. In some embodiments, the ends have a plug and socket configuration (see Figures). The interfaces may have complementary/mirror image geometry, such that multiple conduit ends, if present, can mate with one another the conduits may be surrounded by walls configured to form an airtight, steamable chamber enclosure when the interfaces are juxtaposed to one another. A gasket may be present to assist in the formation of airtight chamber(s). The interfaces may be rigidly and reversibly connected to one another.

In some embodiments, the method includes some or all of the following steps: In a first step (disconnected mode), the two components of the chamber enclosure are disconnected. In a second step (chamber connected mode) the two chamber enclosure components are rigidly juxtaposed, thereby forming an airtight chamber seal. In some embodiments, this is accomplished by an impetus resulting from activation of a linear (force) actuator, e.g., a component configured to transmit a linear force. Linear actuators may be, for example, pneumatic actuators (see FIG. 10) or electrical actuators (see FIG. 15). The two conduit ends remain detached in this step. In a third step (steam sterilization), steam is brought into the chamber. In some embodiments, this is accomplished via steam routing channels, which may be disposed in a manifold block (see FIG. 11). This sterilizes the chamber (s). In a fourth step (fluidic connected mode), the two conduit ends are juxtaposed. In some embodiments, this is caused by further action of the actuator. In some embodiments, when multiple connectors are present, each connection is formed individually. In other embodiments, multiple connections are formed simultaneously. In some embodiments, after the steam sterilization step, the ends are maintained in a sterile environment until after the fluid connection is consummated. In some embodiments, a sterile environment is maintained until the conduit ends are disconnected. A sterile environment refers to an environment that has been sterilized and is kept within an airtight enclosure.

Apparatuses and methods described herein are illustrative. Apparatuses and methods in accordance with this disclosure will now be described in connection with the figures, which form a part hereof. The figures show illustrative features of apparatus and method steps in accordance with the principles of this disclosure. It is to be understood that other embodiments may be utilized and that structural, functional and procedural modifications may be made without departing from the scope and spirit of the present disclosure.

The steps of methods may be performed in an order other than the order shown or described herein. Embodiments may omit steps shown or described in connection with illustrative methods. Embodiments may include steps that are neither shown nor described in connection with illustrative methods.

Illustrative method steps may be combined. For example, an illustrative method may include steps shown in connection with another illustrative method.

Apparatuses may omit features shown or described in connection with illustrative apparatuses. Embodiments may include features that are neither shown nor described in connection with the illustrative apparatus. Features of illustrative apparatus may be combined. For example, an illustrative embodiment may include features shown in connection with another illustrative embodiment.

FIG. 1 depicts a side view of a prior art bioreactor system, including passive component 102 and active component 103. Passive component 102 contains bioreactor vessel housing medium 106 and is connected to active component 103 via prior art connectors 105 and connecting tubes 109. Active component 103 contains peristaltic pumps 107 and user interface 108.

Figure 2:
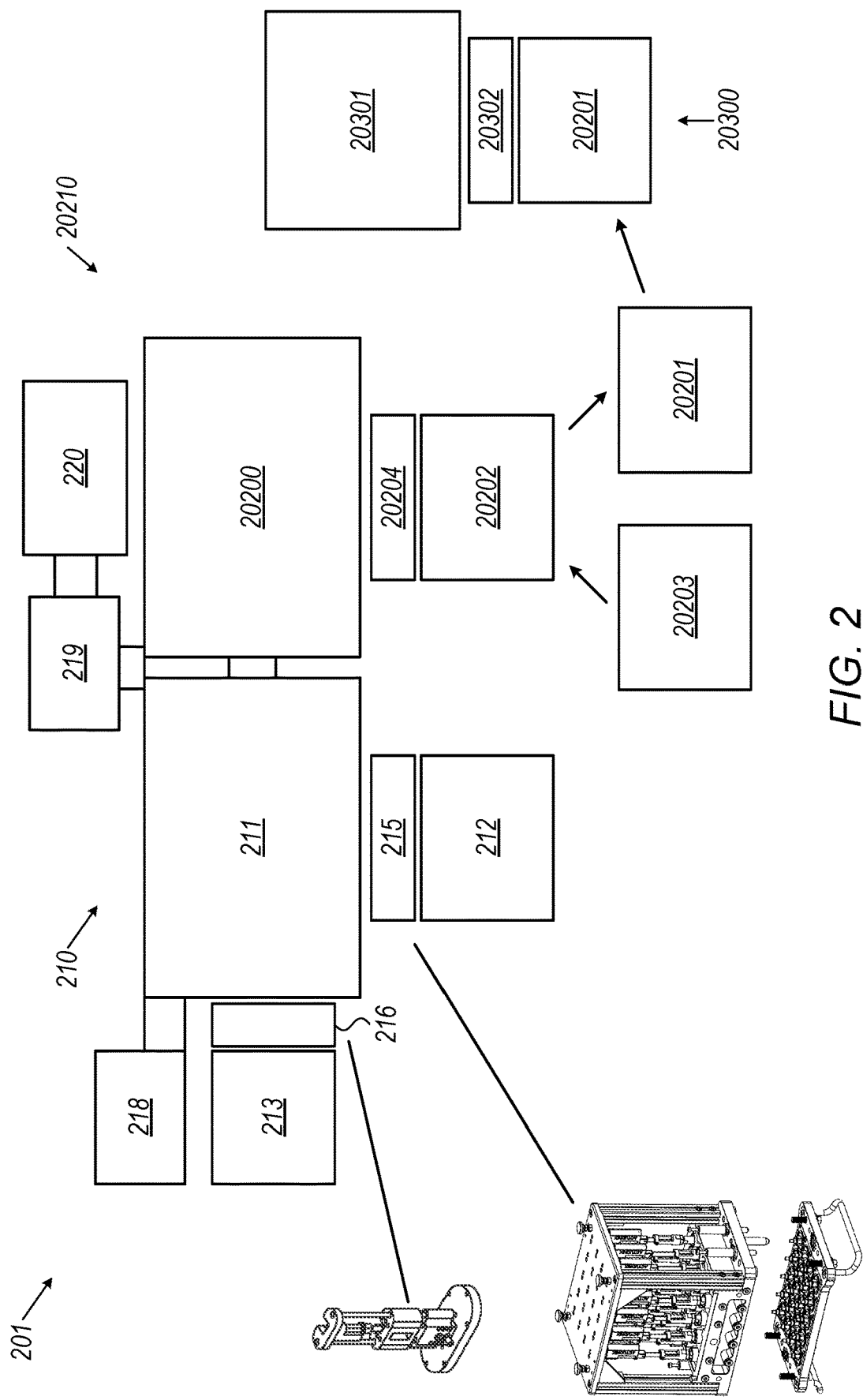
FIG. 2 is a schematic system architecture overview.

FIG. 2 is a schematic system architecture overview in accordance with principles of the disclosure. System 201 includes first (upstream) apparatus or compartment 210 and second (downstream) apparatus or compartment 20210. First apparatus includes central (sub)compartment 211, which may be fixed in place and contains bioreactor chamber (not depicted). First apparatus connects to "slow" upstream module 212 (also referred to as "peripheral compartment") and "fast" upstream module 213 (also referred to as "additional peripheral compartment"), containing fluid containers (not depicted), via slow module interface 215 and fast module interface 216, respectively. Central compartment 211 also may connect to utility lines 218 (depicted schematically by box), such as gas, steam, and cleaning fluid (not depicted). Upstream compartment 210 and/or downstream compartment 20210 may be connected to power/data lines 219, which in turn may connect to supervisory control and data acquisition system 220. Central (sub) component 20200 of downstream compartment 20210 may connect sequentially to downstream modules 20201-20203 via downstream interface 20204. Module handling system 20300, including Reuse (Clean/Sterilize/Fill) Station 20301 can be used to clean any of downstream modules 20201-20203 (depicted for downstream module 20201) via cleaning interface 20302.

Figure 3:
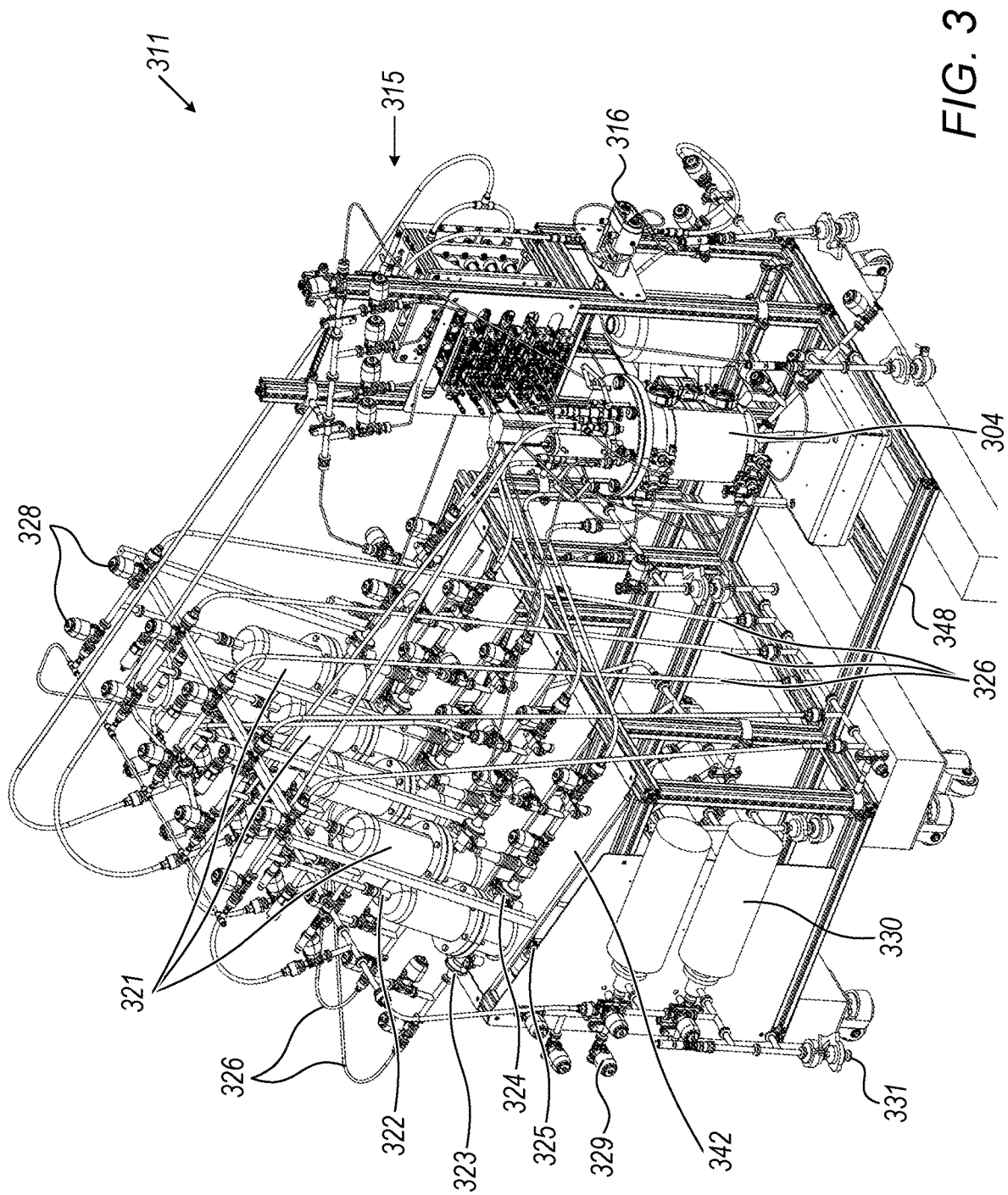
FIG. 3 shows a perspective cutaway view of a central compartment of a described system.

FIG. 3 shows a perspective cutaway view of central compartment 311 of upstream compartment or apparatus, in accordance with principles of the disclosure. Sterile air filters 321 are connected via air lines 326, which can carry air or steam for sterilization, to an upstream pressure regulator (see FIG. 9). This regulator sets and maintains the inlet air pressure to induce air flow through the filter. Temperature and pressure are measured using sensors (see FIG. 6). Each sterile air filter 321 has a vent 322 an inlet 323, an outlet 324, and a drain 325. Valves 328 are placed at each of these ports to control flow through different paths through or around the filter. The flow path depends on whether an automated sterilization protocol or process protocol is being run. Bioreactor 304, attachment sites of slow 315 and fast 316 modules are also depicted. Sterile air filters 321 and associated apparatus are attached to and supported by rigid baseplate 342. Depicted components are attached to and organized and supported by rigid frame 348.

Filters 321 are steamed through their inlet 323, across the filter membrane (not depicted), and out the outlet 324. The vent 322 and drain 325 may be used for pre-heating air filters 321 and filter integrity testing. The auxiliary utility valves 329 (which can be used for water, cleaning fluid, and steam) and equipment are used to route steam into the system from optional preliminary filtration apparatus 330, and route condensate out of the system through a system of system drains 331. Pipes may be angled for optimal draining.

The bioreactor 304 may rest on a scale (see FIG. 4) to continuously or periodically monitor the mass inside the bioreactor. As fluid is added or samples are removed from the bioreactor, its mass will change, from which the flow rate and mass transfer can be deduced.

"Slow", or fixed addition module (shown in detail in later figures; also referred to as "peripheral compartment") may be a mechanism for connecting modules in a manner that maintains the sterility of the steam sterilized station. The "Fast Addition" or "additional peripheral" module interface 315 may serve to attach smaller modules for quick, small additions to the bioreactor. These module(s) can also be used to take samples. They are a smaller version of the slow module, and they may be intended to allow small modules to be attached and removed more often than the slow module. The Fast Addition module may be steam-sterilized and actively water cooled to speed up the connection/disconnection process.

Figure 4:
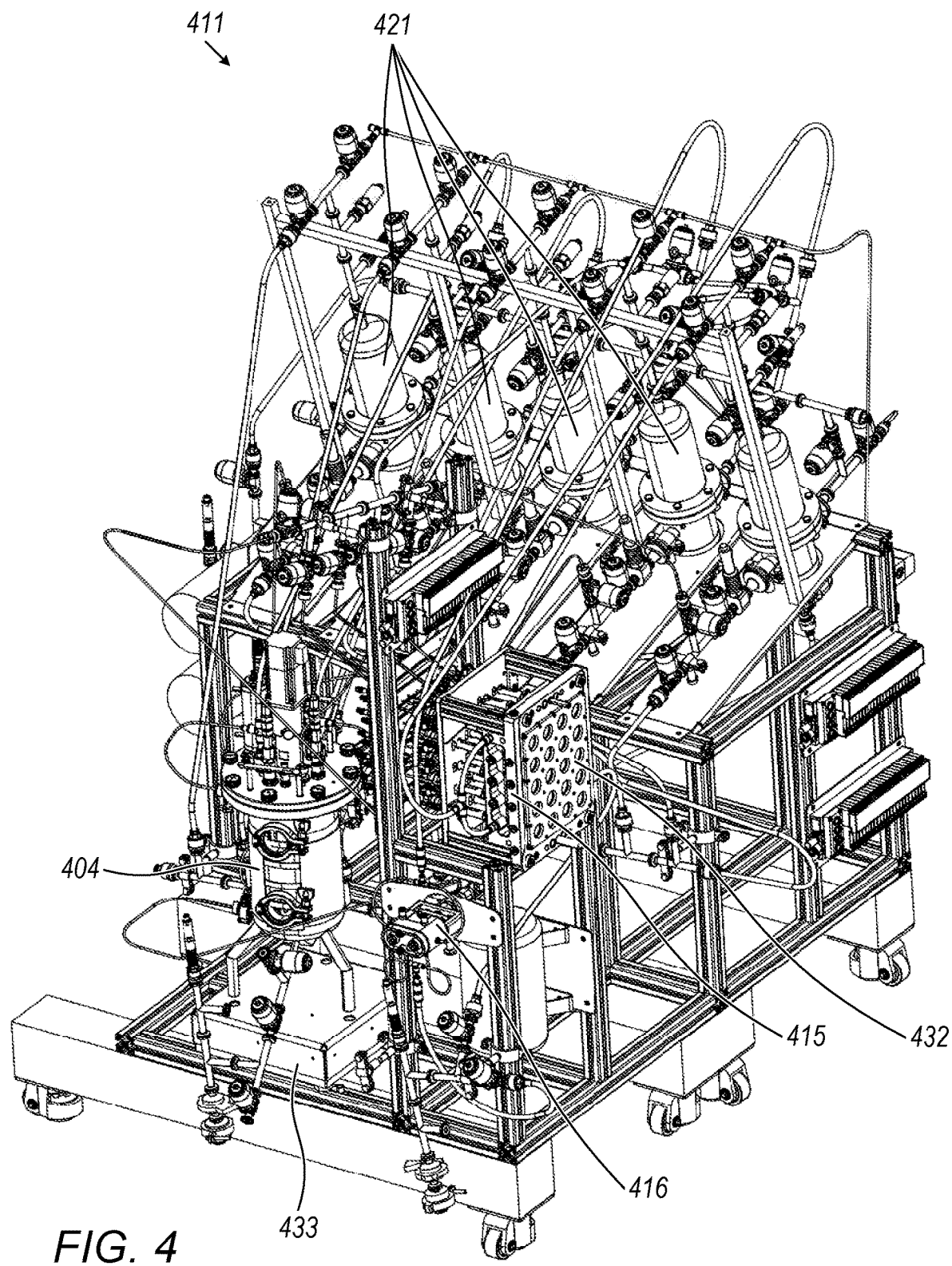
FIG. 4 shows a perspective cutaway view of a central compartment of a described system.

FIG. 4 shows a perspective cutaway view of central compartment 411 of upstream compartment or apparatus, rotated 90 degrees clockwise (when viewed from the top), in a horizontal plane, relative to FIG. 3, in accordance with principles of the disclosure. Slow Addition module is removed, exposing the gasket seal 432 which is used to seal the steam chambers (not depicted) before steaming upon connection (shown in later figures). Bioreactor 404, filters 421, and bioreactor scale 433 are also depicted.

FIG. 5 is a schematic diagram of air flow for making additions to and taking samples from the described bioreactor, in accordance with principles of the disclosure. For making additions, filtered pressurized air is pushed through an interface(s) into reagent tanks, which drives fluid to flow into the bioreactor (top series). For the sampling process, air is supplied through sterile filters into the bioreactor, moving fluid from the reactor across one of the interfaces and into a sample tank (bottom series). Depicted are outgoing pressure line 510, incoming pressure line 512, outgoing fluid line 520, and incoming fluid line 522.

Figure 6:
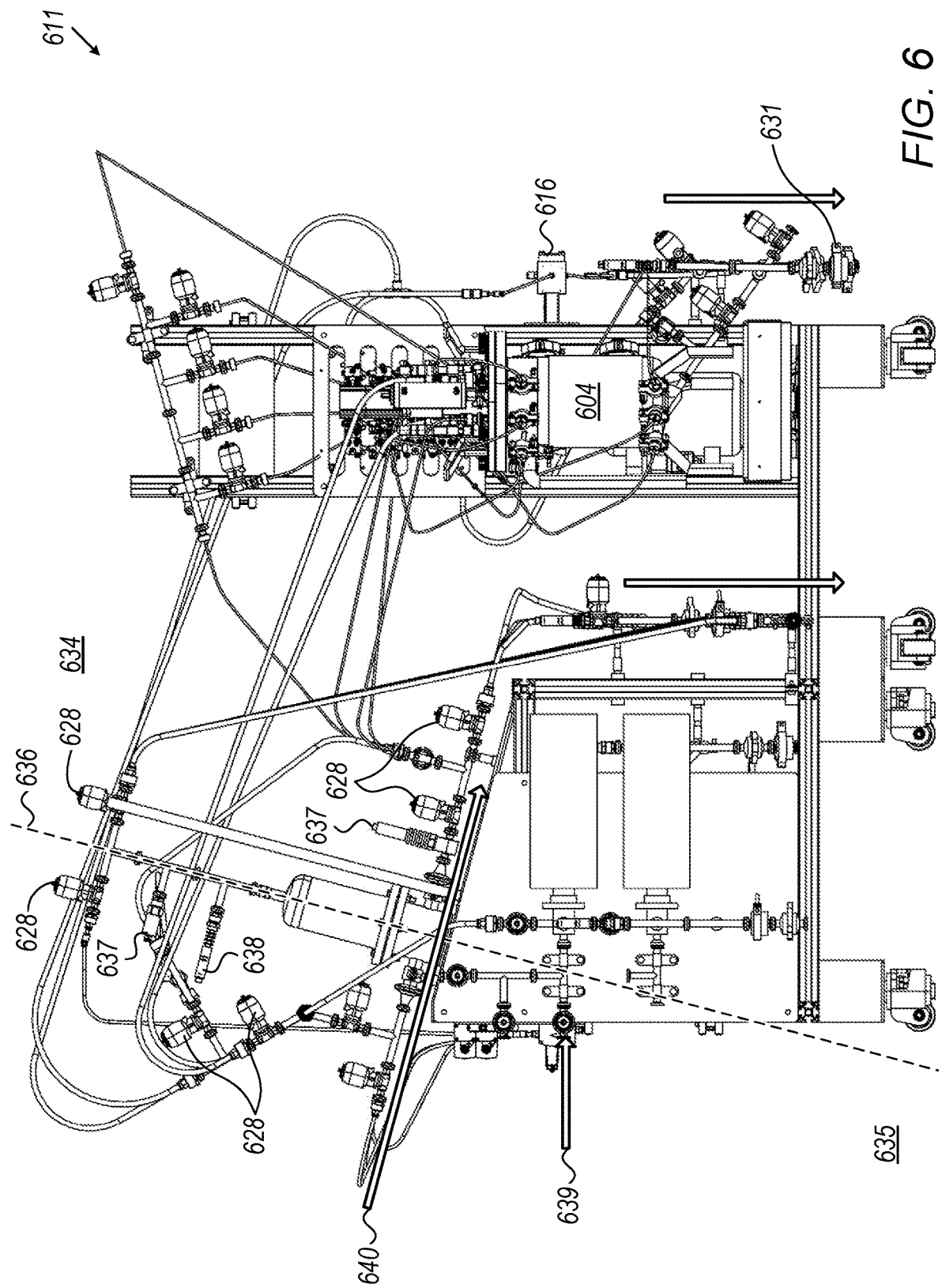
FIG. 6 depicts a side view of a central compartment of a described system.

FIG. 6 depicts a side view of central compartment 611 of upstream compartment or apparatus, highlighting the separation between sterile air side 634 and non-sterile air side 635, created by sterile filter membrane (demarcated by dotted line 636), in accordance with principles of the disclosure. The sterile filter does not allow microbes to pass through its membrane, maintaining sterility on the sterile air side. The sterile boundary is also maintained across our two interfaces, which are depicted in later figures. Fast addition interface 616, valves 628, system drains 631, pressure 637 and temperature gauges 638, and main steam inlet 639 are also depicted. Diagonal arrow 640 shows air flow direction. Vertical arrows show condensation flow direction.

Figure 7:
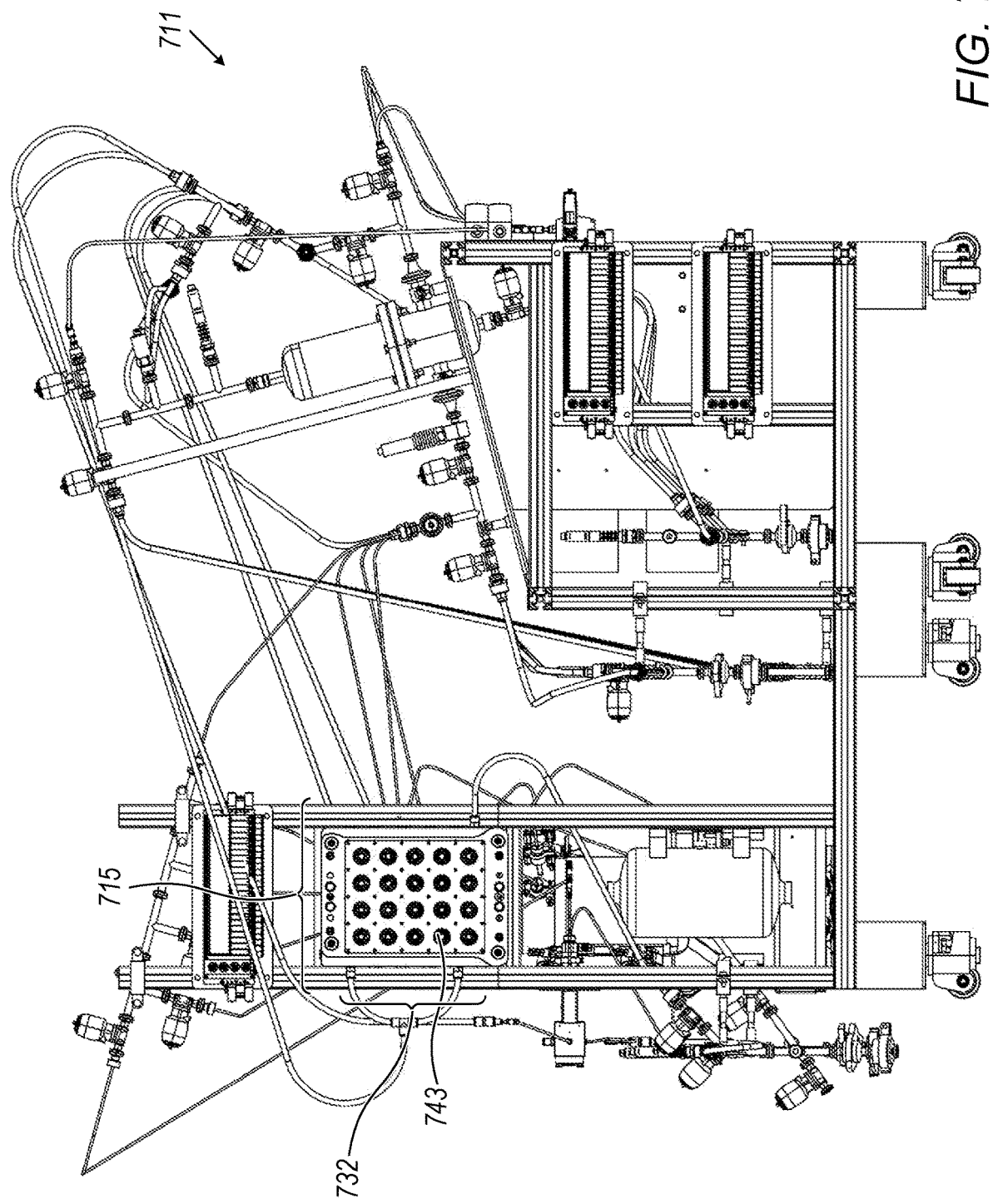
FIG. 7 depicts a side view of a central compartment of a described system, rotated 180 degrees in a horizontal plane relative to FIG. 6.

FIG. 7 depicts a side view of central compartment 711 (also referred to as "station") of upstream compartment or apparatus, rotated 180 degrees in a horizontal plane relative to FIG. 6, in accordance with principles of the disclosure. FIG. 7 depicts the "Slow" peripheral compartment (also referred to as "module") interface 715 without a module connected, revealing gasket seal 732 of the interface 715, forming an airtight seal for steam sterilizing the connection chambers formed between the central compartment (shown here) and the "Slow" peripheral compartment side (depicted in later figures). Attachment of a (pre-sterilized, closed) module (not depicted) to interface 715 forms up to 20 sealed chambers (depicted in later figures), one around each fluidic connector pair (depicted in later figures), each pair including central-side connector 743. The chambers are then steam sterilized, bringing the pre-sterilized module across the sterile boundary of the pre-sterilized station without contaminating either sterile, closed system.

Figure 8:
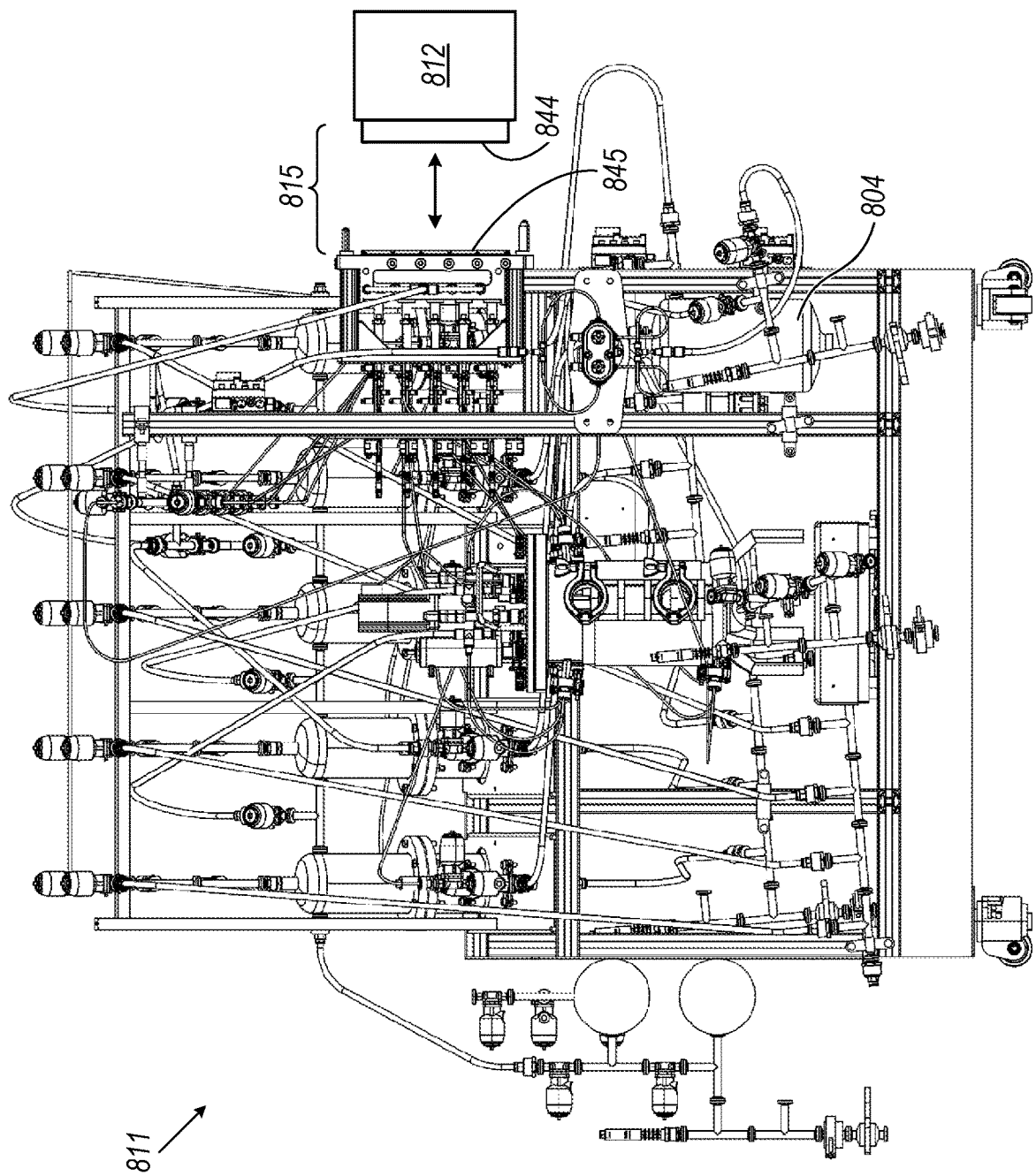
FIG. 8 depicts a front view of a central compartment of a described system, rotated 90 degrees counterclockwise (when viewed from the top) in a horizontal plane relative to FIG. 7.

FIG. 8 depicts a front view of central compartment 811 (also referred to as "station") of upstream compartment or apparatus, rotated 90 degrees counterclockwise (when viewed from the top) in a horizontal plane relative to FIG. 7, in accordance with principles of the disclosure. FIG. 8 depicts the direction of attachment of mating of peripheral side or edge 844 of "slow" interface 815 with central side or edge 845 of "slow" interface 815, which rigidly connects peripheral compartment 812 (schematically depicted as a box; also referred to as "slow module") to central compartment 811. Fluid tanks (not depicted) inside peripheral compartment 812 are connected via tubing (not depicted) to connectors which mate to central compartment 811 within connection chambers within interface 815. Connectors and connection chambers are depicted in later figures. After peripheral compartment 812 is fluidically connected to bioreactor 804 central compartment 811, valves may be used to control air and fluid flow.

Figure 9:
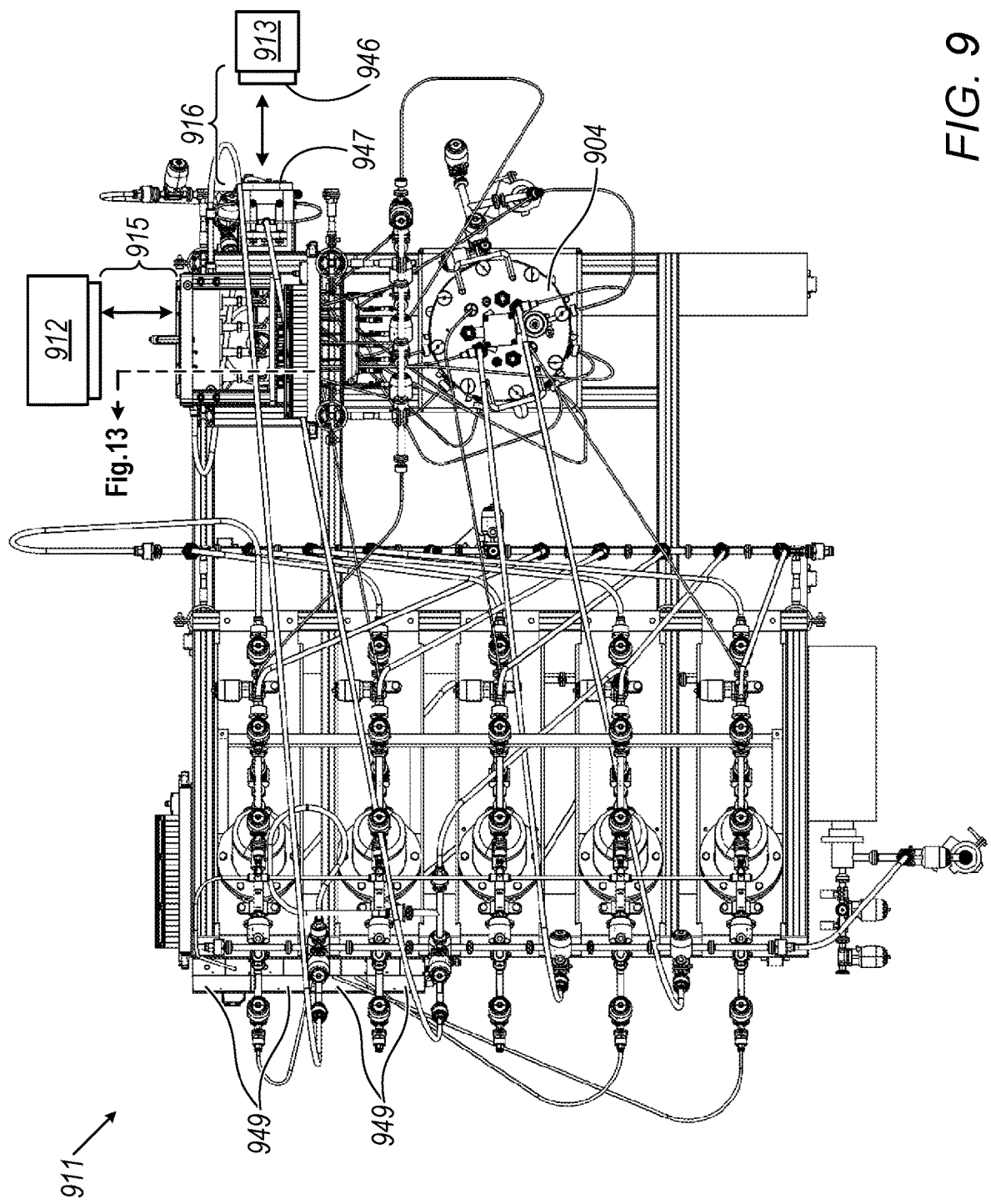
FIG. 9 depicts a top view of a central compartment of a described system.
Figure 13:
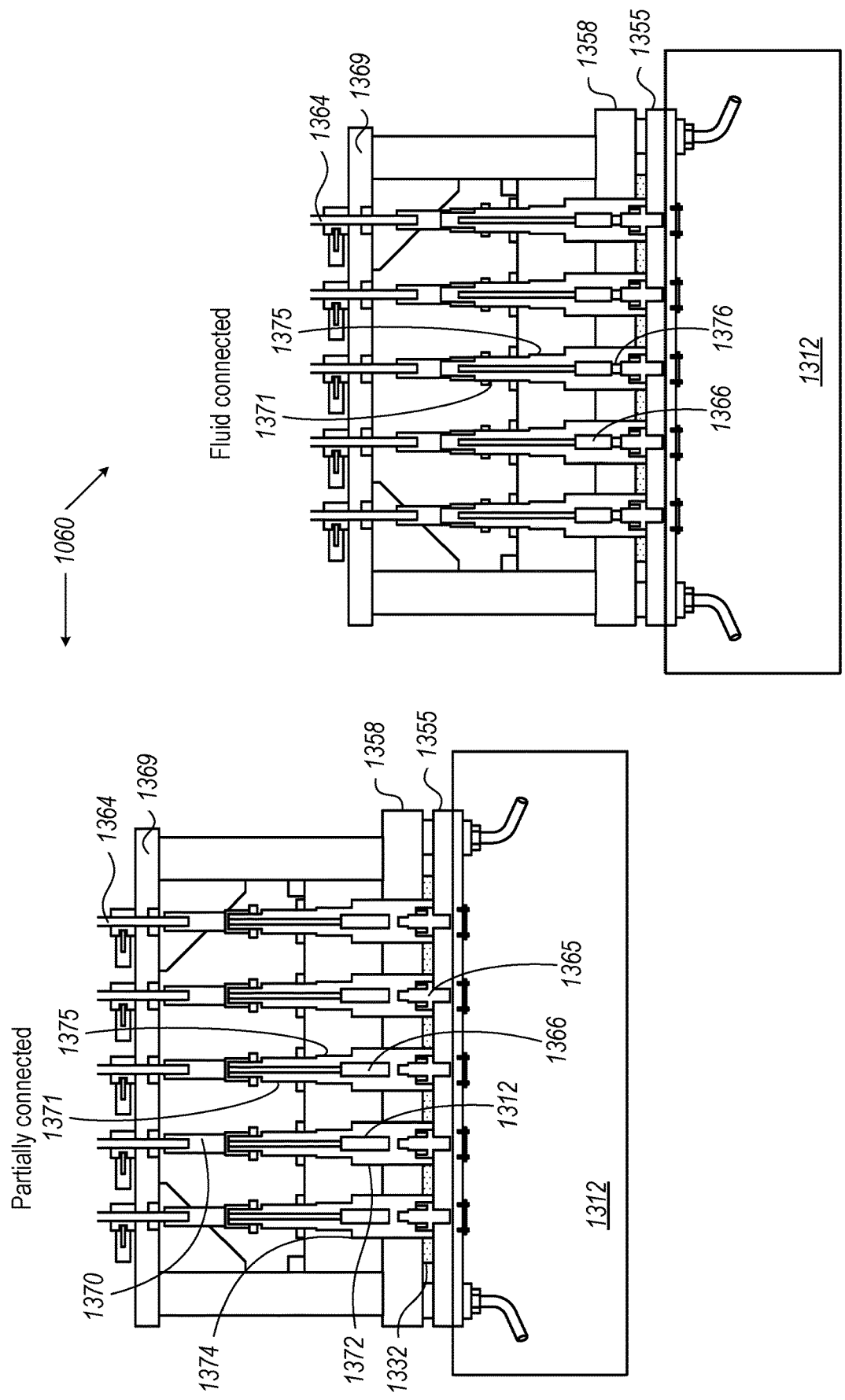
FIG. 13 depicts a side view of a central side component of a described interface and its connection to a peripheral compartment.

FIG. 9 depicts a top view of central compartment 911 showing the direction of attachment at peripheral-side interface 815 and additional peripheral-side interface 816 (also referred to as "fast addition"), in accordance with principles of the disclosure. Additional peripheral-side interface 816 may attach in a similar fashion to slow addition interface. The peripheral side 846 of fast addition module 813 mates with the central side 847 of the module to form a sealed chamber around its two fluid connectors. Double-headed arrows show vector of motion when attaching or detaching modules. Connection chambers are steamed to sterilize the connections, thus joining the modules with the station while maintaining the sterility of each. Connectors and connection chambers are depicted in later figures. Pressure regulators 949 are also depicted. A cross-section of the bracketed area is shown in FIG. 13.

Figure 10:
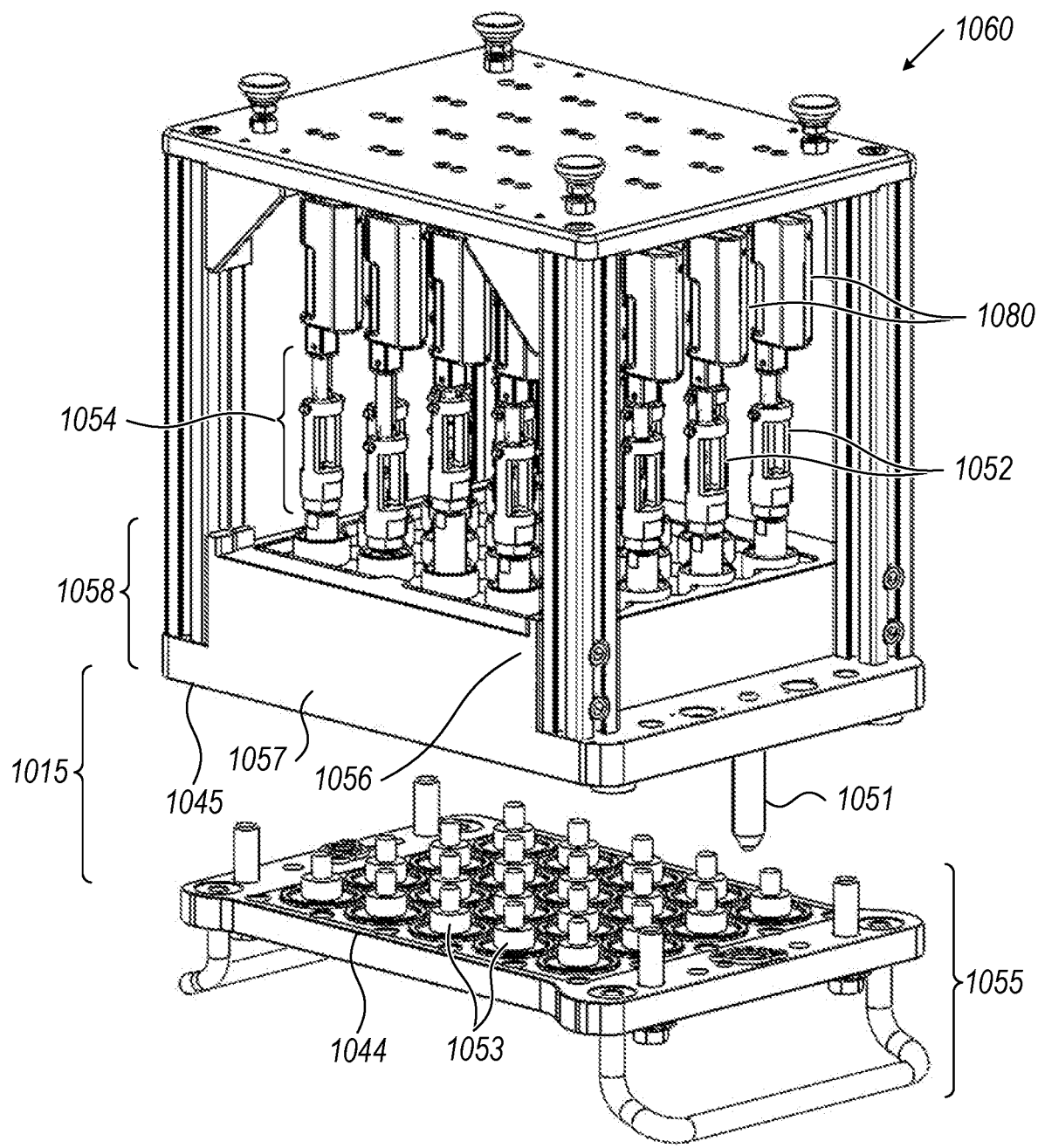
FIG. 10 depicts a perspective, cutaway view of a steamable interface, including arrayed connectors.

FIG. 10 depicts a perspective, cutaway view of a steamable interface including arrayed connectors, showing a possible array arrangement 1054 of central-side connectors 1052 and linear actuators 1080 of central side component 1060 of slow module interface 1015, in accordance with principles of the disclosure. Attachment may be guided by 1-2 alignment pins, one of which, 1051, is visible in this view. Alignment pin 1051 and central-side connector termini (not visible) protrude from interface-side edge 1045 of central side component 1060. Central-side connectors 1052 are anchored in steam chamber block (also referred to as "central-side plate") 1058, for which proximal 1056 and distal 1057 sides are depicted. Peripheral-side connectors 1053 are anchored in peripheral plate 1055 and protrude from interface-side peripheral edge 1044 of peripheral plate 1055.

Figure 11:
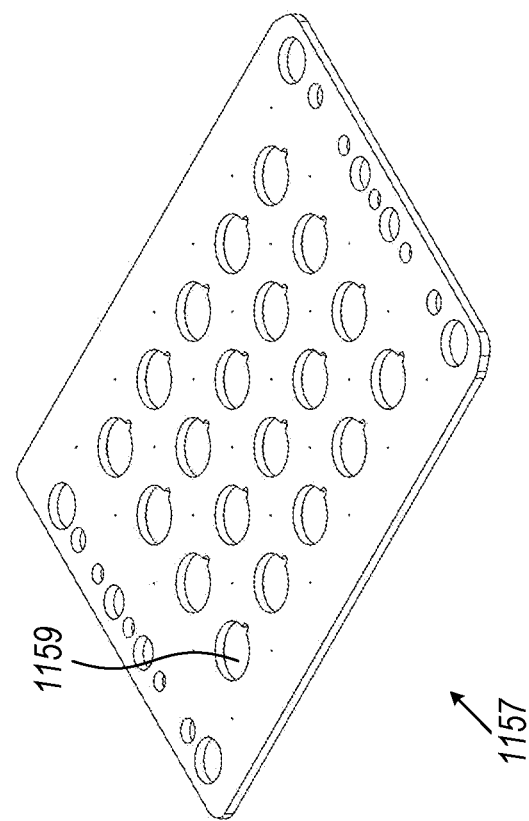
FIG. 11 shows a disassembled, cross-sectional view of proximal and distal plates of a described steam chamber block.
Figure 11:
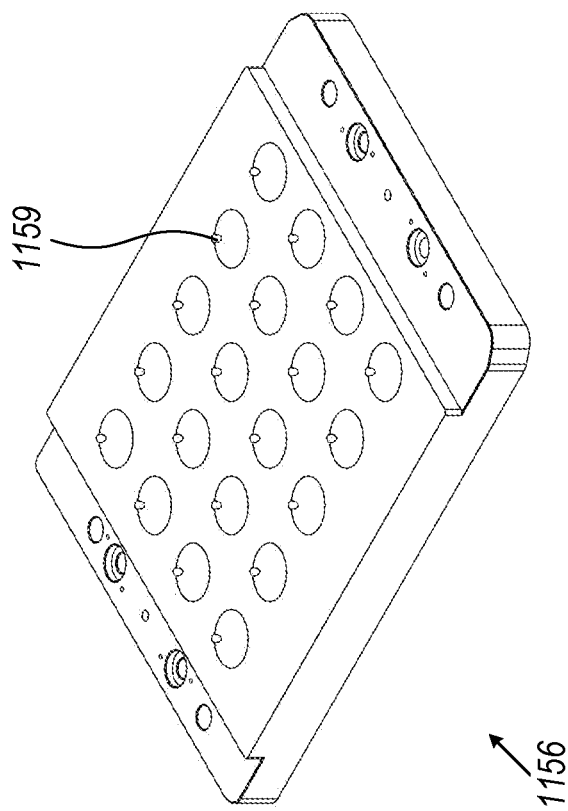

FIG. 11 shows a cross-sectional view, in the plane of connection and transverse to the direction of liquid flow (not depicted), in which steam chamber block (shown assembled in FIG. 10) is bisected into proximal 1156 and distal 1157 sides, with distal side 1157 flipped both vertically and horizontally, such that right edges of distal side 1157 (proximal to alignment pin 1051 in FIG. 10) appears on left side in FIG. 11, in accordance with principles of the disclosure. Steam routing channels 1159 of steam chamber block are depicted.

Figure 12:
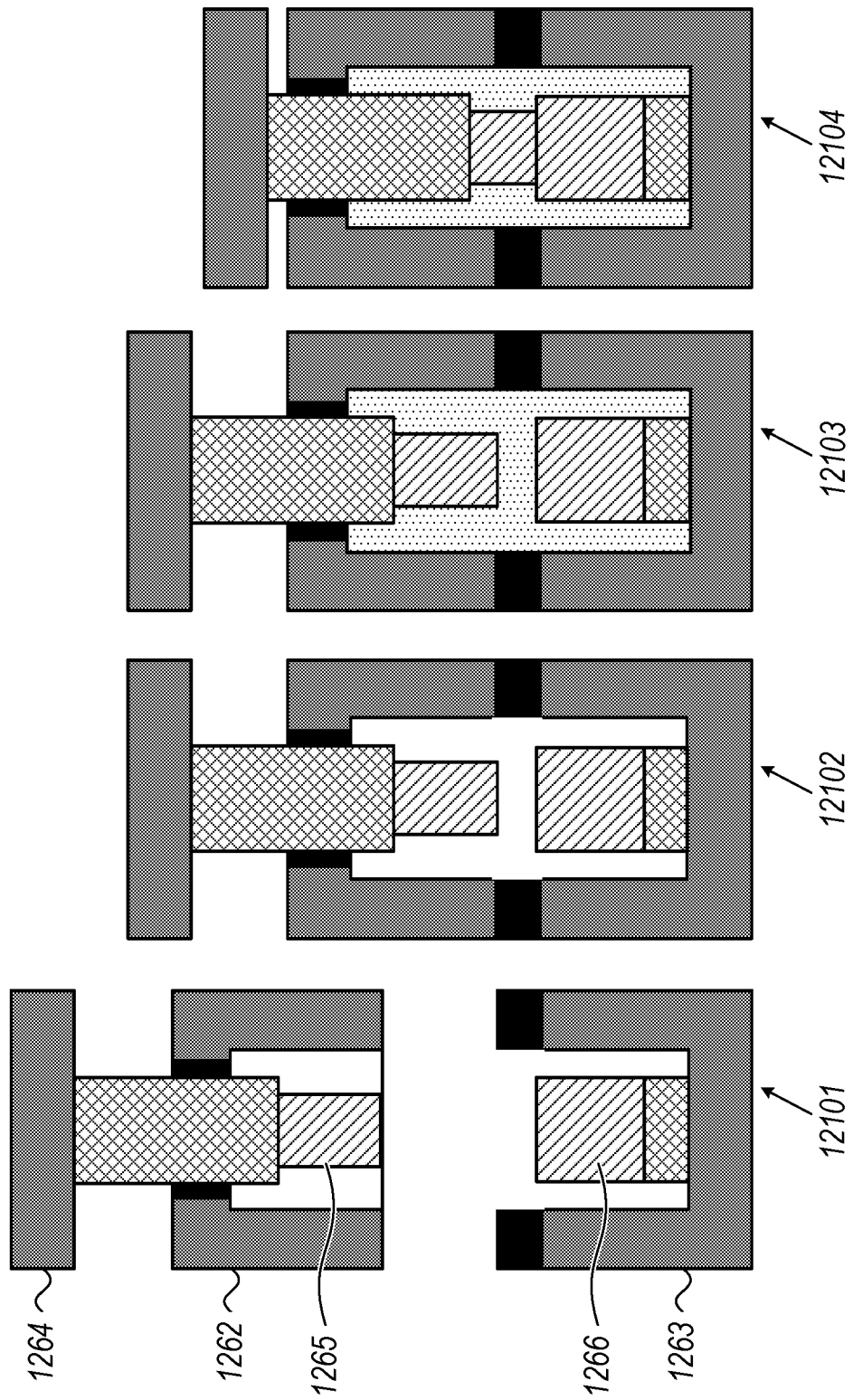
FIG. 12 is a schematic depiction of a described 4-step interface connection and sterilization process.

FIG. 12 is a schematic depiction of a 4-step interface connection and sterilization process, in accordance with principles of the disclosure. Components are depicted schematically. In step 1/disconnected mode 12101, two halves of chamber enclosure, namely center-side 1262 and peripheral-side 1263 chamber enclosure components, are disconnected. In step 2/chamber connected mode 12102, center-side 1262 and peripheral-side 1263 chamber enclosure components are juxtaposed by action of actuator linear 1264, thereby forming airtight chamber seal, while fluid connector plug 1265 and socket 1266 remain detached. In step 3/steam sterilization 12103, steam is pumped into system via steam routing channels (see FIG. 11), thereby sterilizing chamber. In step 4/fluidic connected mode 12104, plug 1265 and socket 1266 fluid connectors are juxtaposed by further action of actuator 1264 to form fluid connection.

FIG. 13 depicts a side view of the central side component 1060 of an interface and its connection to a peripheral compartment (which may be also referred to as "slow module"), depicted schematically as box 1312, in accordance with principles of the disclosure. Actuator 1364 traverses central-side plate 1369 via apertures (not depicted) and rigidly connects to coupler 1370, which in turn rigidly connects to piston 1371 and chamber housing 1372. Directions of motion of linear actuator 1364 and (future) fluid/air flow path are represented by 2-headed arrows. Prior to chamber-connected mode, peripheral plate 1355 has been placed and rigidly secured (for example, with bolts [not depicted]) against gasket seal 1332. Peripheral plate 1355 may have been pre-sterilized separately, e.g., in an autoclave.

In chamber-connected mode (left panel; paralleling step 2 of the previous figure), actuator 1364 has engaged coupler 1370 and exerted force to move coupler 1370 to an intermediate downward position, with piston 1371 and chamber housing 1372 moving downward accordingly. By virtue of this downward motion, lower edge 1373 of chamber housing 1372 traverses gasket seal 1332 and presses against peripheral plate 1355, thus forming a closed and airtight steam chamber 1374. Steam chamber 1374 is maintained in closed position via piston seal 1375. Fluid connector plug 1365 and socket 1366 remain detached from one another.

In the next step (not depicted; paralleling step 3 of the previous figure), steam chamber 1374 is steam-sterilized through chambers formed by the peripheral plate 1355 and (central-side) steam chamber block 1358. Steam is routed through steam chamber block 1358 from several inlets (not depicted).

In fluid-connected mode (right panel; paralleling step 4 of the previous figure), actuator has fully engaged downward to move fluid connector plug 1365 downward, thus mating with socket 1366 to form fluid connection 1376. Fluid connections 1376 may be simultaneously or independently actuated.

Figure 14:
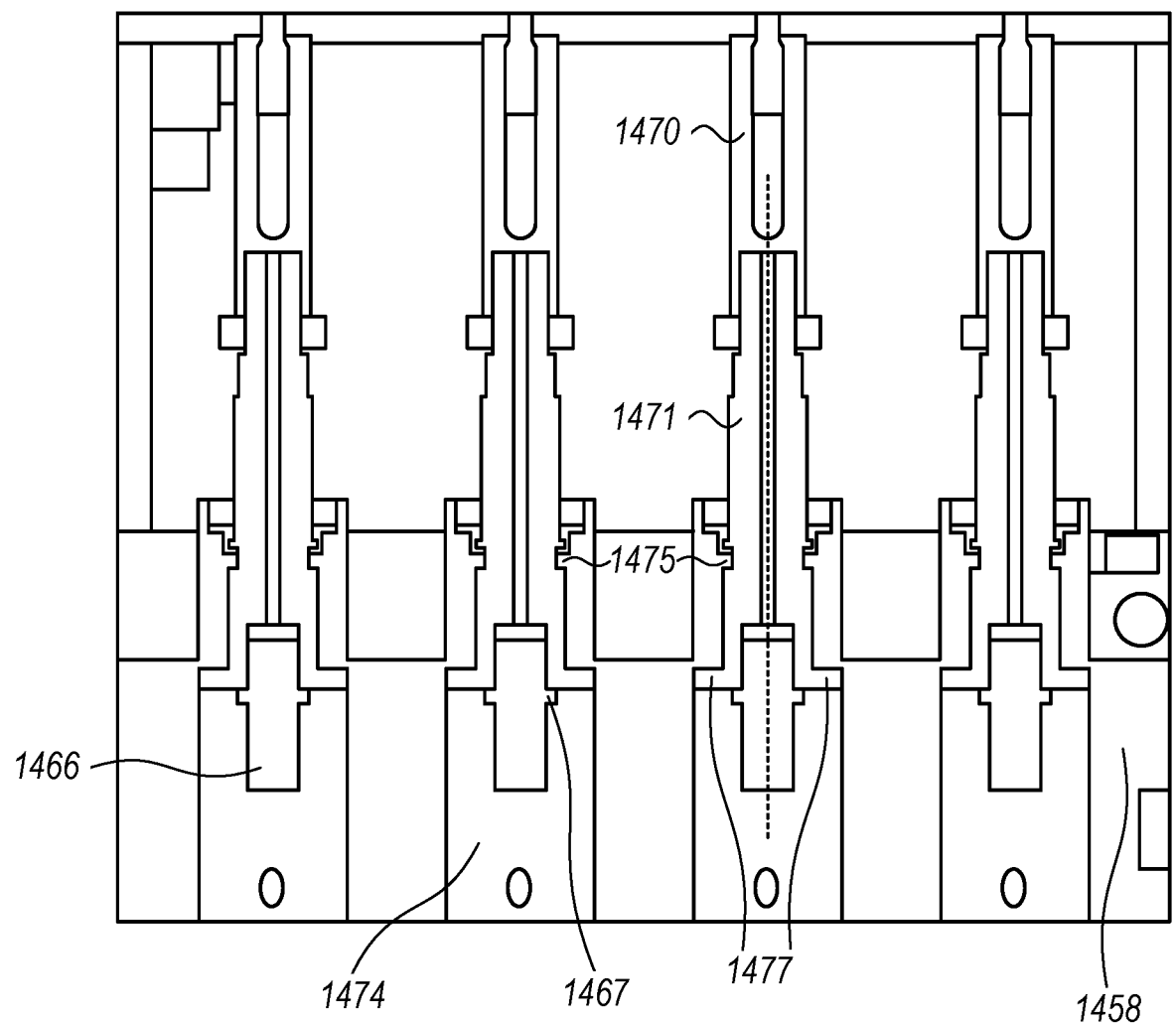
FIG. 14 depicts a magnified view of the coupling apparatus of the central side component shown in FIG. 13.

FIG. 14 depicts a magnified view of the coupling apparatus of the central side component shown in FIG. 13, in fully retracted (disconnected) position, showing couplers 1470, piston 1471, steam chamber block 1458, socket 1466, including protruding portion 1467, and piston seal 1475, which seals the interface between upper piston and steam chamber block. Dotted line depicts fluid flow path. Piston distal edge 1477 abuts both steam chamber 1474 and socket protruding portion 1467 to form a steam-tight seal.

Figure 15:
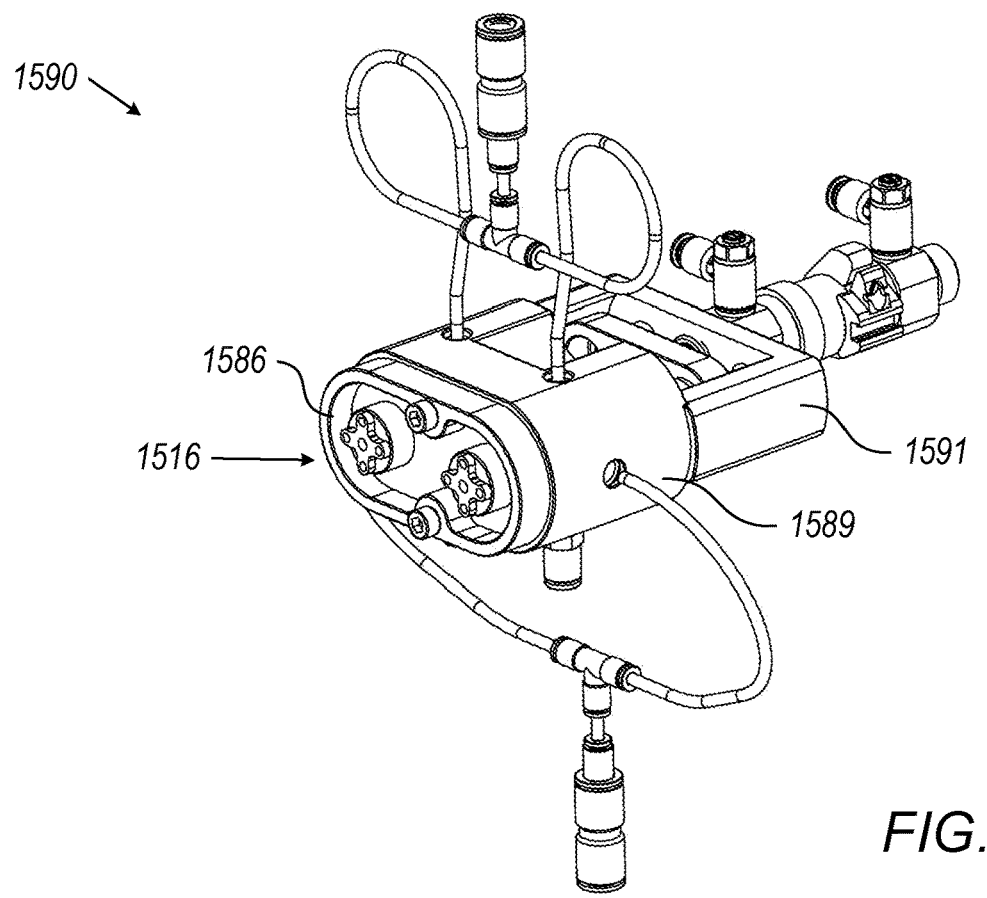
FIG. 15 depicts a perspective view of a described connecting apparatus, including a central side component of an interface and components disposed proximally thereto.

FIG. 15 depicts a perspective, isolated view of the central side component 1590 of interface 1516 for additional peripheral compartment (also referred to as "fast module interface"), in accordance with principles of the disclosure. Depicted are fast module gasket seal 1586, chamber housing block 1589, and actuator mount 1591. The mechanism of attachment of fast module and its individual connectors may be similar to that of slow module.

Figure 16:
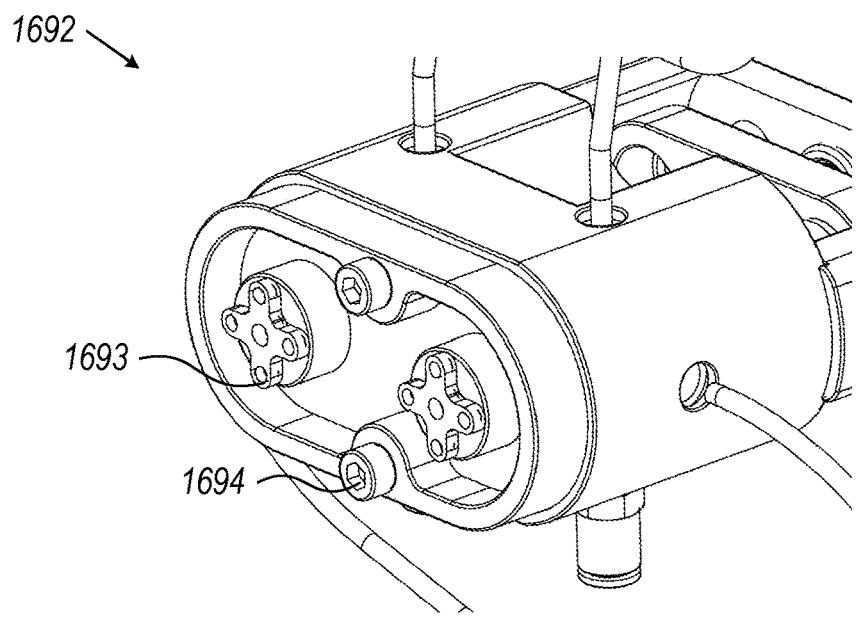
FIG. 16 depicts a perspective, isolated view of a central side component of a described system.

FIG. 16 depicts a perspective, isolated view of distal end 1692 (relative to the central compartment) of central side component 1660 of interface 1616 for additional peripheral compartment (also referred to as "fast module interface"), in accordance with principles of the disclosure. Depicted are apertures 1693 for bolts (not depicted) for securing individual connection interfaces, and apertures 1694 for bolts for securing module connection interface.

Figure 17:
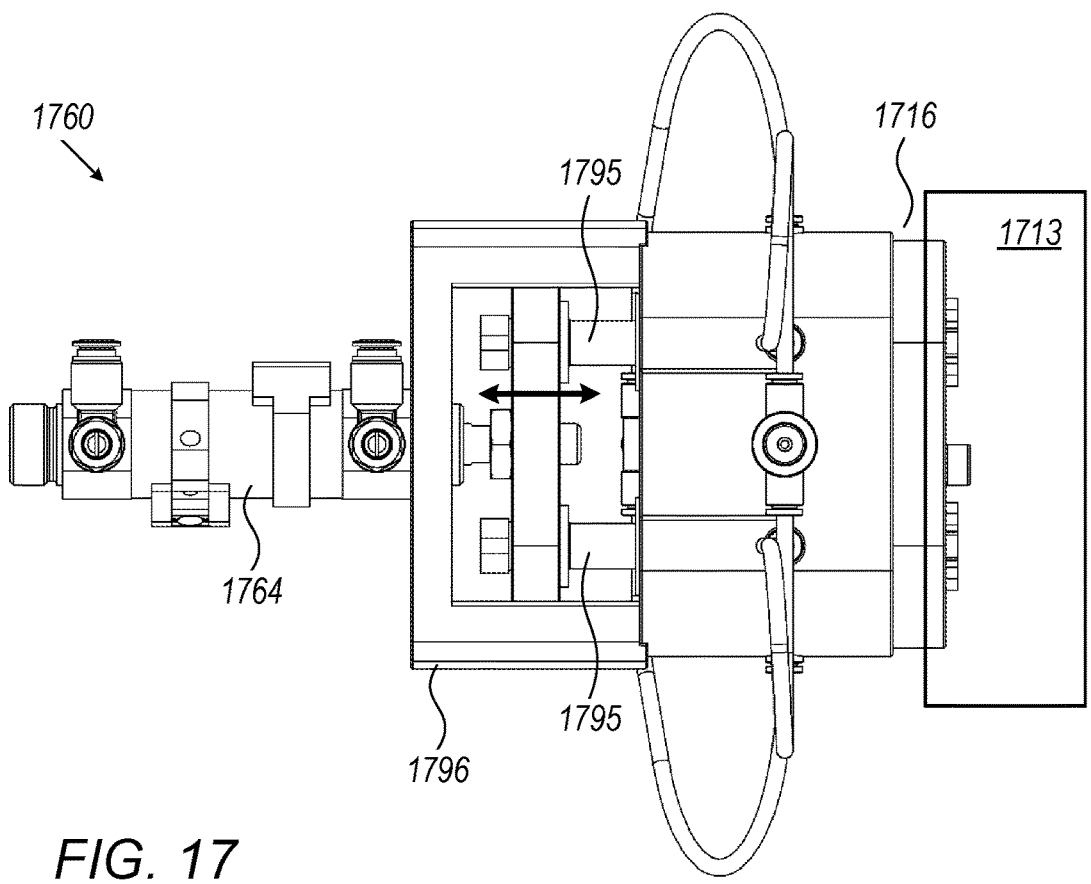
FIG. 17 depicts a perspective, isolated view of a distal end of a central side component of a described interface.

FIG. 17 depicts a top view of central side component 1760 of interface 1716 for additional peripheral compartment (also referred to as "fast module interface"), in accordance with principles of the disclosure. Proximal ends 1795 of fluid connectors and linear actuator 1764 are depicted. Proximal end 1796 of central side component 1760 may be rigidly connected to remainder of central compartment, for example by attachment to a plate (not depicted) mounted on a rigid frame. Fast module is depicted schematically by box 1713. Two-headed arrow denotes direction of motion of linear actuator 1764.

Figure 18:
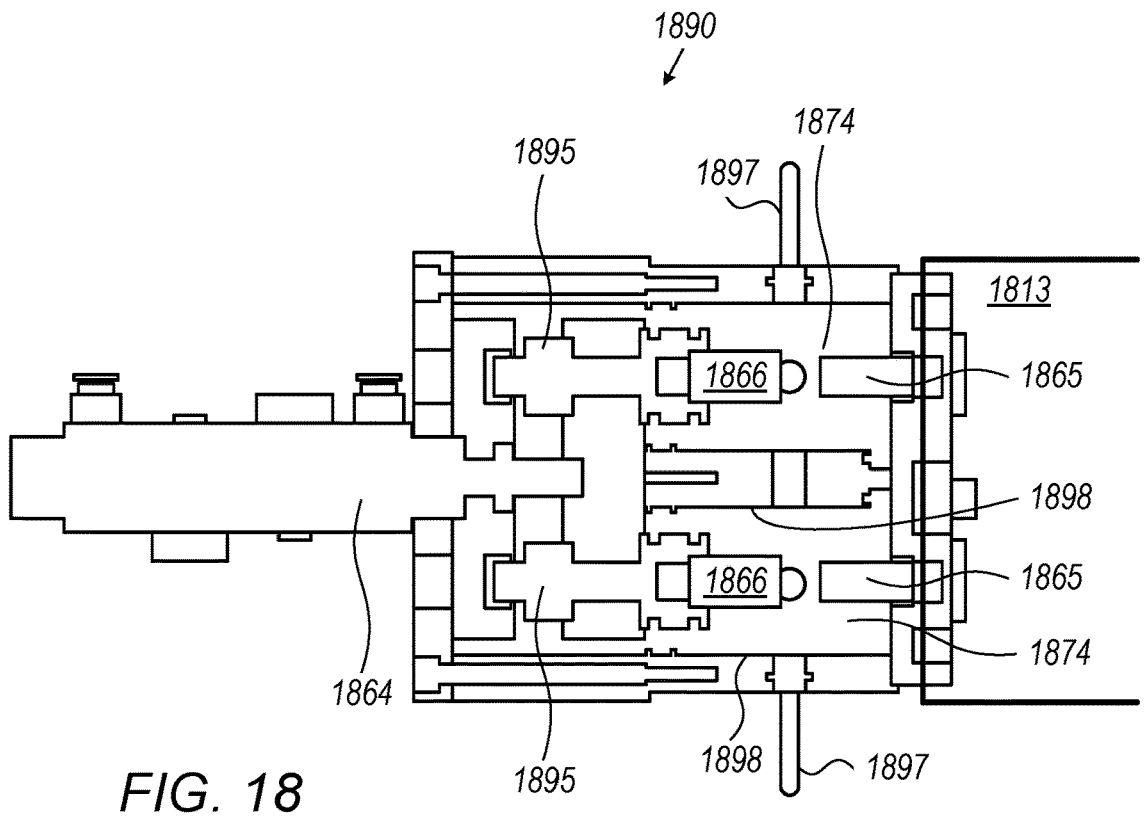
FIG. 18 depicts a top view of a central side component of a described interface.

FIG. 18 depicts a top, cross-sectional view, sectioned longitudinally through the steam chambers 1874, of central side component 1890 of interface for additional peripheral compartment (also referred to as "fast module interface"), in accordance with principles of the disclosure. Steam chambers 1874 are depicted in chamber-connected, but fluid-disconnected, position/mode, in which fluid connector plugs 1865 and sockets 1866 are separated. Fast module 1813 is depicted schematically as a box. Proximal ends 1895 of fluid connectors are depicted. Two-headed arrow denotes direction of motion of linear actuator 1864. Tubing 1897 is described for the next figure (see description of peripheral inlet line). When fast module 1813 is connected to central side component 1890, fluid connector plugs 1865 insert into lumen of steam chambers 1874. Subsequent force provided by linear actuator 1864 moves fluid connector sockets 1866 rightward, causing them to mate with plugs 1865 as depicted in FIGS. 12 and 13. Cooling channels (not depicted) approximately one millimeter in diameter surround outer edges 1898 of steam chambers 1874, acting as a water jacket to enable rapid cooling after steam sterilization.

Figure 19:
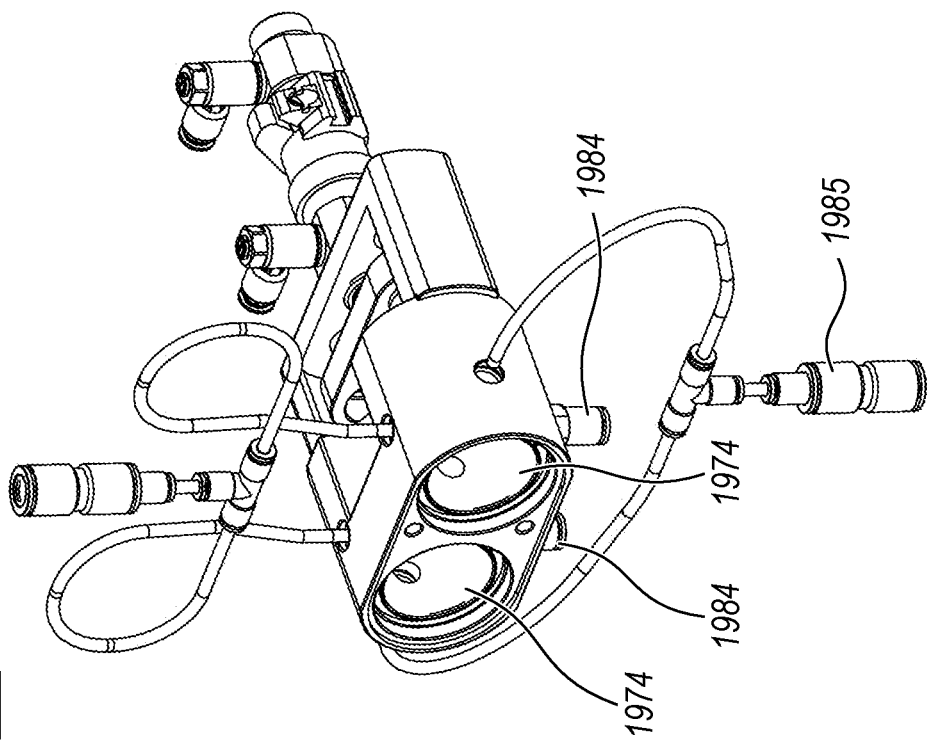
FIG. 19 depicts a top, cross-sectional view of a central side component of a described interface.

FIG. 19 depicts a perspective, isolated view of the central side component 1990 of fast module interface, attached to linear actuator, in accordance with principles of the disclosure. Cutaway view, with fast module gasket seal removed, enables visualization of steamable connection chambers (also referred to as "steam chambers") 1974.

Cooling inlet/outlet tubes 1984 enable circulation of water from a pump (not depicted) through cooling channels (see description of previous figure). Steam inlet connectors 1985 are also depicted.

Figure 20:
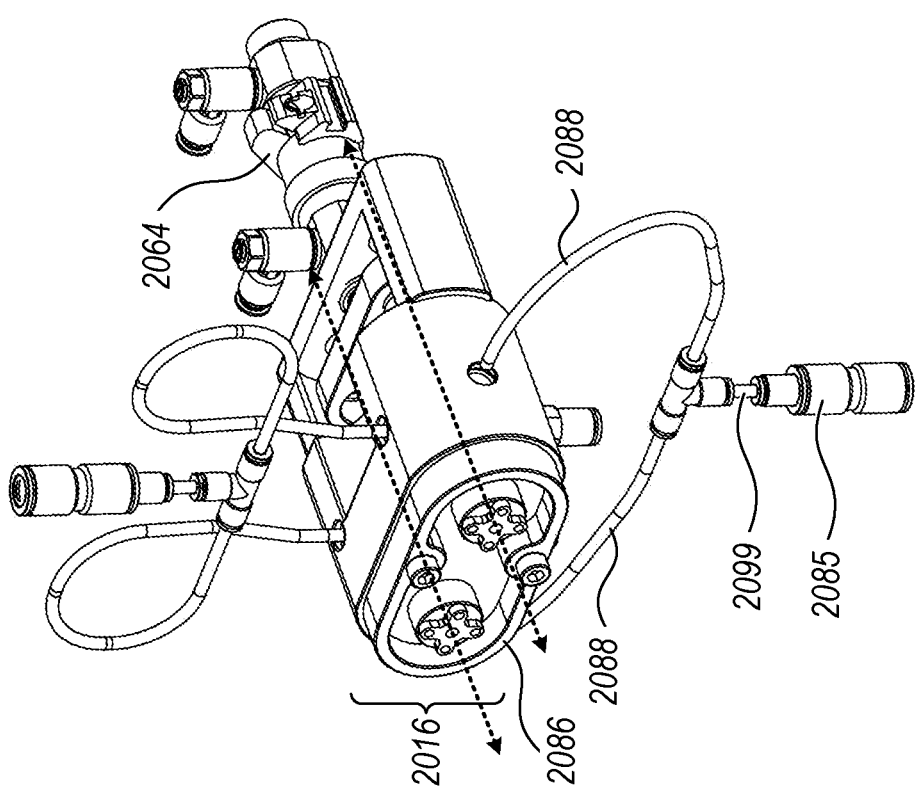
FIG. 20 depicts a perspective, isolated view of a central side component of a described interface, attached to an actuator.

FIG. 20 depicts the same apparatus with fast module gasket seal 2086 attached.

Steam for sterilization first passes through a single inlet line 2099, which splits into two peripheral inlet lines 2088, one for each steam chamber 2074. Steam exits via chamber steam outlet tubing. The two steam chambers 2074 are connected internally (connection not visible in this view) to maintain balance during steaming.

Fluid flow through the interface 2016 is depicted by dotted lines. Fluid paths within central side component 2090 are not visible in this view.

Figure 21:
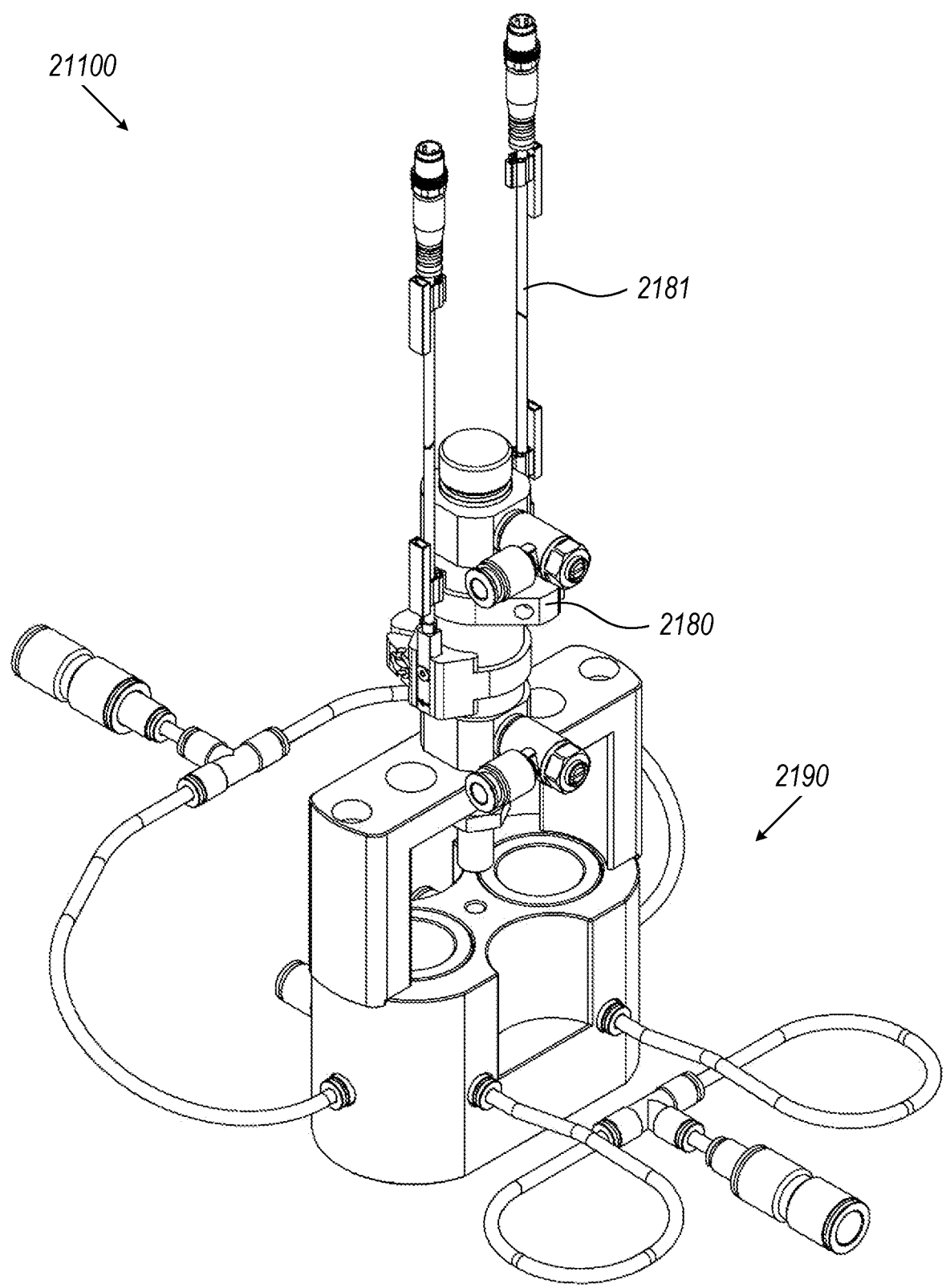
FIG. 21 depicts a perspective view of a described connecting apparatus, including a central-side interface component and components disposed proximally thereto.

FIG. 21 depicts a perspective view of "fast" connecting apparatus 21100, including the central-side component 2190 of fast module interface and components disposed proximally (internally) thereto, including actuators 2180 and actuator sensor cables 2181, in accordance with principles of the disclosure.

Figure 22:
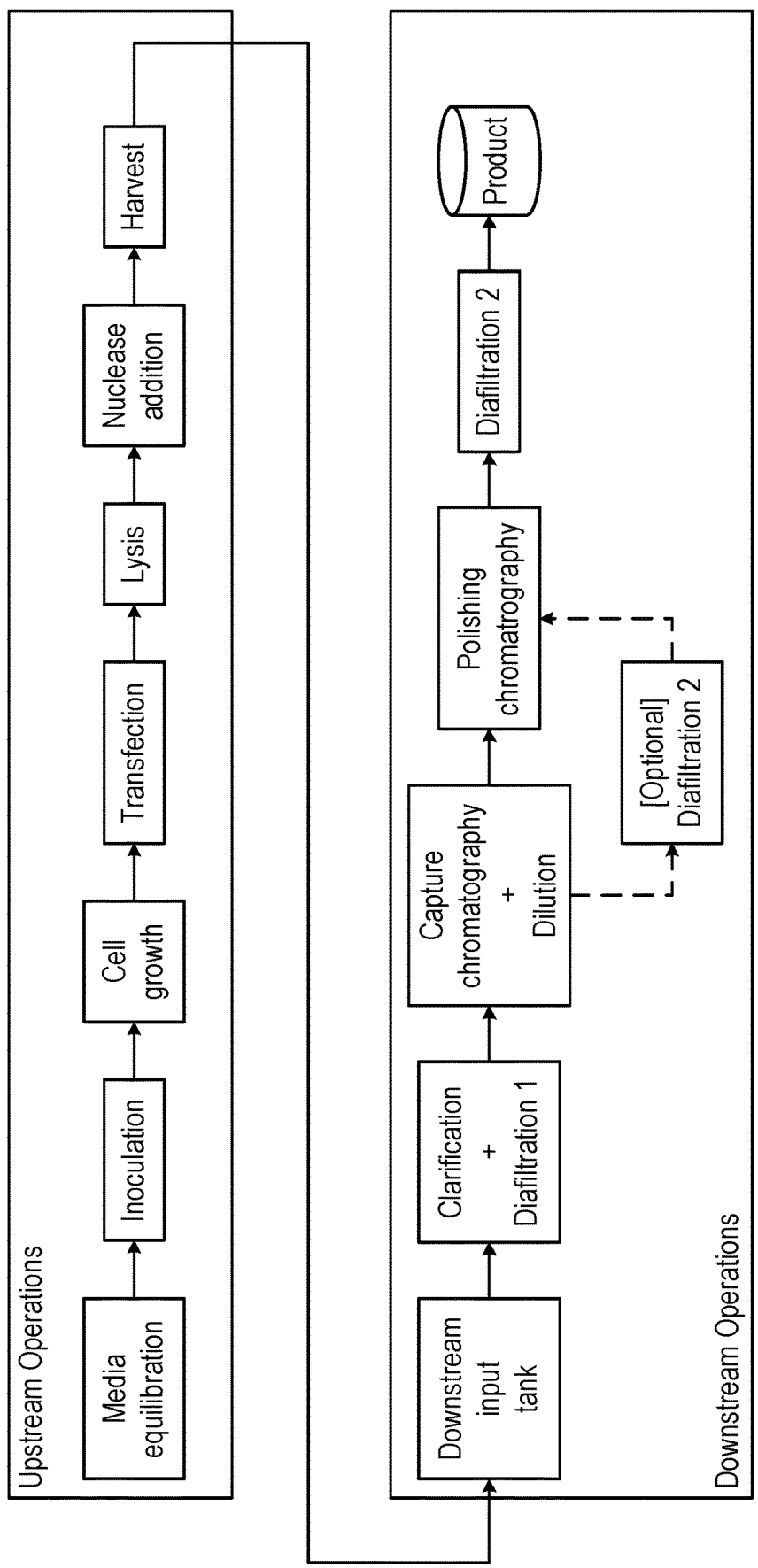
FIG. 22 is a flow chart depicting a consolidated method for growing, harvesting, and purifying virus particles.

FIG. 22 is a flow chart depicting an exemplary consolidated method for growing, harvesting, and purifying virus particles, in accordance with principles of the disclosure.

In step 1, Media Equilibration, the bioreactor is clean, sterile, and ready to run with the "slow addition" module attached. Media is added, and conditions in the reactor (temperature, pH, dissolved oxygen [$DO_2$]) are equilibrated and controlled.

In step 2, Inoculation, cells are added to the bioreactor manually using the "fast addition" module.

In step 3, Cell Growth, bioreactor conditions continue to be maintained to promote cell growth. Cells expand to desired density. This step typically continues for 3-10 days.

In step 4, Transfection, plasmid and transfection reagent are added via the "fast addition" module to initiate viral transfection. This step typically continues for 1-3 days.

In step 5, Lysis, lysis buffer is added to initiate breakdown of cells to release viral particles.

In step 6, Nuclease Addition, nuclease is added to digest host cell chromatin.

In step 7, Harvest, product is transferred from bioreactor to hold tank for downstream operations.

In step 8, Clarification+Diafiltration 1, initial lysate filtration is performed, and buffer is exchanged for concentrating buffer compatible with the capture step.

In step 9, Capture Chromatography+Dilution, product is captured via chromatography, and the buffer is subsequently diluted to lower the salt concentration.

In optional step 9B, Supplemental Diafiltration, the diafiltration step is repeated.

In step 10, Polishing Chromatography, empty and full capsids are separated.

In step 11, Final Diafiltration, buffer is exchanged into the final formulation buffer. Product may be concentrated, if required.

Figure 23:
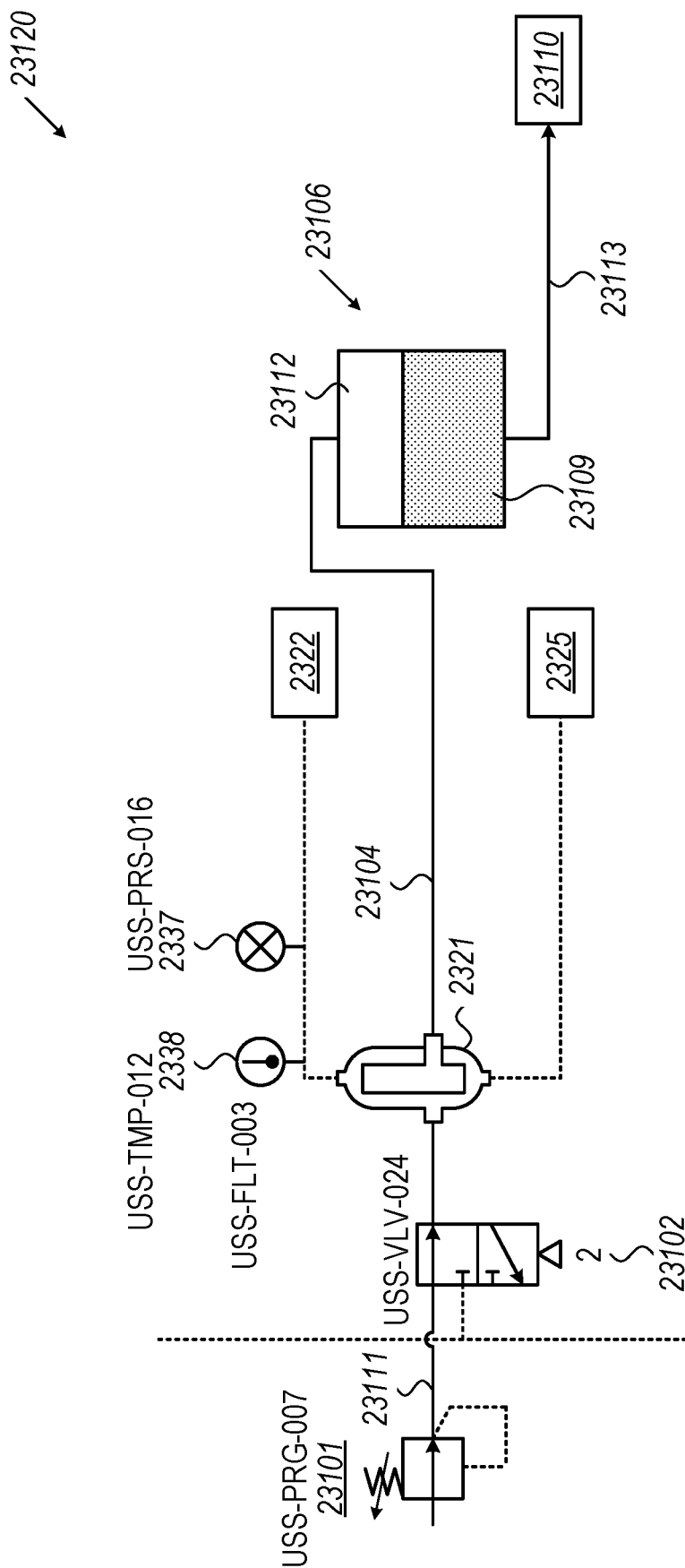
FIG. 23 is a schematic depiction of a described fluid propulsion system for impelling a fluid out of a container.

FIG. 23 is a schematic depiction of a fluid propulsion system 23120 for impelling a fluid out of a container or tank 23016 (which may be also referred to as a "reagent tank"), in accordance with principles of the disclosure. Pressure actuator 23101, which may be a pressure regulator, may be programmatically set to a predetermined pressure level by a controller (not depicted). If the set pressure level is greater than the pressure in proximal air line 23111, which is disposed downstream (right side of diagram) relative to actuator 23101, pressured air flows through proximal air line 23111. If selector valve 23102 is open to air passage, pressurized air proceeds to air sterilizing filter 2321, which is operably connected to vent 2322, drain 2325, pressure sensor 2337, and temperature sensor 2338. Pressurized air proceeds through sterile air line 23104 to head space 23112 of container 23106, which may be a medium reservoir or a reservoir of another liquid reagent (e.g., a reagent needed for a biotechnological process). Increased pressure in head space 23112 impels fluid 23109 (which may be medium or another liquid reagent [e.g., a reagent needed for a biotechnological process]) out of container 23106, through downstream fluid line 23113 into fluid destination container 23110.

Figure 24:
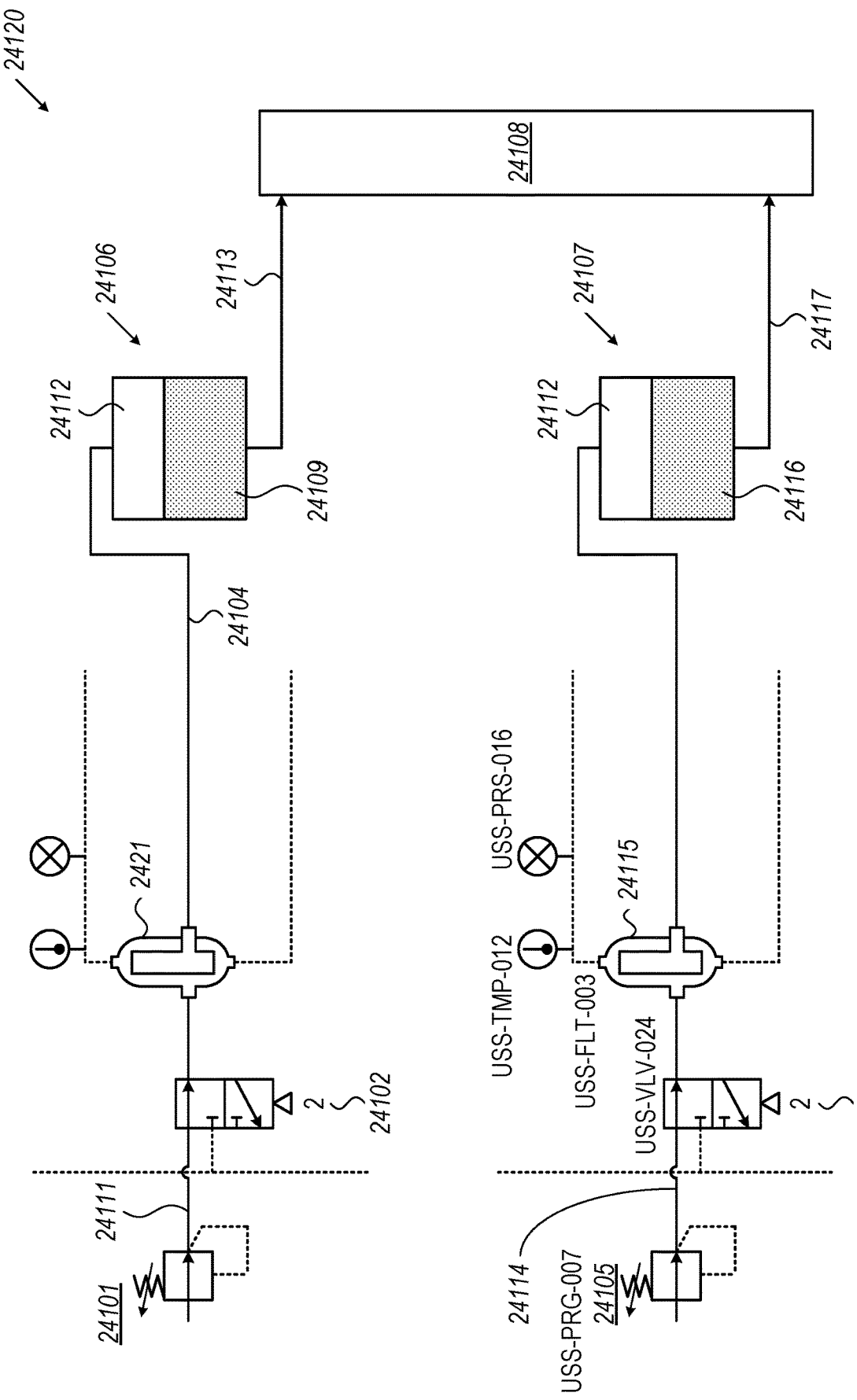
FIG. 24 is a schematic depiction of a described fluid propulsion system.

FIG. 24 is a schematic depiction of a fluid propulsion system 24120, in accordance with principles of the disclosure. Fluid propulsion system 24120 is similar to the system of the previous figures, except that it enables alternating, two-way movement of fluid back and forth through or across a fluid destination with multiple openings, such a filter 24108.

First pressure actuator 24101, which may be a pressure regulator, may be programmatically set to a predetermined pressure level by a controller (not depicted). If the mentioned pressure level is greater than the pressure in first proximal air line 24111, which is disposed downstream relative to first actuator 24101, pressured air flows through first proximal air line 24111. If selector valve 24102 is open to air passage, pressurized air proceeds to air sterilizing filter 2421. Pressurized air proceeds through first sterile air line 24104 to head space 24112 of first reagent tank 24106, which may be a reservoir of a liquid reagent (e.g., a reagent needed for a chemical process). Increased pressure in head space 24112 impels first fluid 24109 (which may be medium or another liquid reagent [e.g., a reagent needed for a chemical process]) out of first reagent tank 24106, through first downstream fluid line 24113 into filter 24108.

To reverse flow of fluid through filter 24108, first pressure actuator is switched to passive (venting) mode, and second pressure actuator 24105, which may be a pressure regulator, is set to a pressure level by a controller. Pressurized air is impelled through second proximal air line 24114 and second air sterilizing filter 24115, into head space 24112 of second reagent tank 24107, which may be a reservoir of a liquid reagent (e.g., a reagent needed for a chemical process), impelling second fluid 24116 through second downstream fluid line 24117 into filter 24108.

The aforementioned components can be utilized in biotechnological and chemical processes, for example those processes described hereinabove. Another exemplary process, for illustrative purposes, is the following:

Step 1: The central compartment is cleaned and sterilized via attachment and sterile fluidic connection of specialized modules to the "slow" and "fast" addition interfaces. These modules route fluid from one connector to another via direct conduits (without an intervening tank), enabling movement of cleaning fluid and steam through the system for cleaning and sterilization of the internal lines. The sterile filters are also sterilized in this step. Similar cleaning and steam sterilization steps may be performed for other compartments, as needed during the biotechnological and/or chemical processes performed. These cleaning and sterilization programs are automated. The associated processor is configured to choreograph the necessary steps.

Step 2: Following sterilization, the closed system is maintained in positively pressurized state, to maintain its sterility and isolation from the external environment.

Step 3: Peripheral compartment(s) that will be attached to the central compartment are sterilized either via autoclaving or using a reuse station, e.g., as described hereinabove.

Step 4: Bottles or flasks holding various process liquids required throughout the cell culture process are connected to a plate of a (first) peripheral compartment (also referred to as the "slow module").

Step 5: The peripheral compartment is connected to an interface on the central compartment. This peripheral compartment may remain attached to the central compartment throughout the duration of the desired process.

Step 6: The connection chambers are steam sterilized.

Step 7: The connection chambers are fluidically connected, as necessary to add components to the bioreactor from the various tanks in the peripheral compartment. Growth media is added, and equilibrated while stirring to the desired temperature, dissolved $O_2$ concentration, and pH.

Step 8: An additional ("fast") peripheral compartment or module is attached to the central compartment via an additional interface. Active cooling is used to expedite the connection.

Step 9: The additional interface is used to add an inoculum of mammalian cells to the bioreactor to begin the culture process.

Step 10: The "fast" module is detached from the additional interface are replaced by additional modules, when necessary to take a sample from the bioreactor or add another reagent.

Step 11: pH, dissolved oxygen, and temperature of the bioreactor are continuously or periodically monitored and controlled. Parameters are maintained and adjusted as needed by adding carbon dioxide and sterile air-driven liquid reagents, and using resistive heating blanket. These control loops are automated with pre-programmed parameters.

One of ordinary skill in the art will appreciate that the steps shown and described herein may be performed in other than the recited order and that one or more steps illustrated may be optional.

Thus, methods, systems, and apparatuses products may improve and optimize biotechnological processes, such as cell culture and downstream purification steps. Persons skilled in the art will appreciate that the present invention can be practiced by other than the described embodiments, which are presented for purposes of illustration rather than of limitation.

What is claimed is:

1. An apparatus, comprising:
   A. a central compartment comprising a central-side interface, wherein:
      said central compartment further comprises: (i) one or more pressure actuators; (ii) a plurality of outgoing pressure lines connecting said one or more pressure actuators to said central-side interface; (iii) a bioreactor chamber; and (iv) a plurality of incoming fluid lines connecting said central-side interface to said bioreactor chamber;
      said one or more pressure actuators are configured to transmit pressure along said plurality of outgoing pressure lines; and
      said bioreactor chamber is configured to house living cells and a growth medium;
   B. a peripheral compartment, comprising: (i) a plurality of fluid storage containers; (ii) a plurality of incoming pressure lines; and (iii) a plurality of outgoing fluid lines; wherein:
      each of said plurality of fluid storage containers is operably connected to at least one of said incoming pressure lines and at least one of said outgoing fluid lines;
      each of said plurality of incoming pressure lines is configured to sterilely and reversibly connect to one of said outgoing pressure lines; and
      each of said plurality of outgoing fluid lines is configured to sterilely and reversibly connect to one of said incoming fluid lines.

2. The apparatus of claim 1, wherein said central compartment is configured for sterilization and reuse.

3. The apparatus of claim 1, wherein said peripheral compartment comprises a peripheral-side interface.

4. The apparatus of claim 1, wherein said central compartment further comprises valves.

5. The apparatus of claim 1, wherein said bioreactor chamber has a capacity of 15 liters or less.

6. The apparatus of claim 1, wherein said central compartment further comprises sensors configured to monitor fluid transfers.

7. The apparatus of claim 1, wherein (a) each of said plurality of outgoing pressure lines and said plurality of incoming fluid lines comprises a terminus, collectively central-side termini, said central-side termini being arranged in a first essentially planar array; and (b) each of said plurality of incoming pressure lines and said plurality of outgoing fluid lines comprises a terminus, collectively peripheral-side termini, said peripheral-side termini being arranged in a second essentially planar array; and (c) pairs of said central-side termini and said peripheral-side termini are configured to be enclosed within an enclosure resistant to pathogen entry to one another, and then sterilized and fluidly connected, said pairs being maintained in a sterile environment until after fluid connection therebetween is consummated.

8. The apparatus of claim 1, wherein said central compartment is connected to a utility line configured to provide at least one of a sterilizing medium and a cleaning medium.

9. The apparatus of claim 1, wherein said central compartment further comprises a pressure-driven product sampling line, connecting said bioreactor chamber to a sample container.

10. The apparatus of claim 1, wherein at least one of the fluid storage containers comprises a growth medium.

11. The apparatus of claim 1, wherein at least one of the fluid storage containers comprises a suspension of living cells.

* * * * *